United States Patent
Liu et al.

(10) Patent No.: US 8,017,323 B2
(45) Date of Patent: Sep. 13, 2011

(54) FREE REACTANT USE IN NUCLEIC ACID-TEMPLATED SYNTHESIS

(75) Inventors: David R. Liu, Lexington, MA (US); Kaori Sakurai, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 211 days.

(21) Appl. No.: 11/336,405

(22) Filed: Jan. 20, 2006

(65) Prior Publication Data

US 2006/0223086 A1    Oct. 5, 2006

Related U.S. Application Data

(60) Provisional application No. 60/646,584, filed on Jan. 21, 2005.

(51) Int. Cl.
*C12Q 1/68* (2006.01)
*C12P 19/34* (2006.01)

(52) U.S. Cl. .......................... 435/6; 435/91.2
(58) Field of Classification Search .................. None
See application file for complete search history.

(56) References Cited

U.S. PATENT DOCUMENTS

| | | | |
|---|---|---|---|
| 4,683,202 A | 7/1987 | Mullis | |
| 4,863,857 A | 9/1989 | Blalock et al. | |
| 5,162,218 A | 11/1992 | Schultz | |
| 5,270,170 A | 12/1993 | Schatz et al. | |
| 5,449,602 A | 9/1995 | Royer et al. | |
| 5,516,940 A | 5/1996 | Katti et al. | |
| 5,539,082 A | 7/1996 | Nielsen et al. | |
| 5,547,835 A | 8/1996 | Koster | |
| 5,550,019 A | 8/1996 | Reed | |
| 5,559,000 A | 9/1996 | Janda et al. | |
| 5,573,905 A | 11/1996 | Lerner et al. | |
| 5,574,141 A | 11/1996 | Seliger et al. | |
| 5,597,697 A | 1/1997 | Diamond | |
| 5,601,800 A | 2/1997 | Katti et al. | |
| 5,605,798 A | 2/1997 | Koster | |
| 5,622,824 A | 4/1997 | Koster | |
| 5,637,682 A | 6/1997 | Nieuwlandt et al. | |

(Continued)

FOREIGN PATENT DOCUMENTS

DE    196 46 372 C1    11/1996

(Continued)

OTHER PUBLICATIONS

Balachander et al. (Langmuir, 1990, vol. 6, No. 11, p. 1621-1627).*

(Continued)

*Primary Examiner* — Stephanie K Mummert
(74) *Attorney, Agent, or Firm* — Goodwin Procter LLP

(57) ABSTRACT

The present invention provides methods and compositions for expanding the scope of chemical reactions that can be performed during nucleic acid-templated organic syntheses. In particular, nucleic acid-templated chemistries are used to produce reaction intermediates attached to an oligonucleotide that can be used to identify the reaction intermediates and/or the resulting reaction products. The reaction intermediates then are reacted with free reactants (for example, reactants that are difficult or impractical to couple to an oligonucleotide) to produce a reaction product. This approach expands the scope of reagents useful in nucleic acid-templated syntheses to reagents that do not need to be or cannot be tethered to an oligonucleotide. The reagents, however, still permit the synthesis of reaction products attached to oligonucleotides that can be used to identify the reaction products.

17 Claims, 12 Drawing Sheets

U.S. PATENT DOCUMENTS

| | | | |
|---|---|---|---|
| 5,639,603 | A | 6/1997 | Dower et al. |
| 5,660,988 | A | 8/1997 | Duck et al. |
| 5,677,195 | A | 10/1997 | Winkler et al. |
| 5,691,141 | A | 11/1997 | Koster |
| 5,698,685 | A | 12/1997 | Summerton et al. |
| 5,708,153 | A | 1/1998 | Dower et al. |
| 5,719,262 | A | 2/1998 | Buchardt et al. |
| 5,721,099 | A | 2/1998 | Still et al. |
| 5,723,289 | A | 3/1998 | Eaton et al. |
| 5,723,598 | A | 3/1998 | Lerner et al. |
| 5,770,358 | A | 6/1998 | Dower et al. |
| 5,770,367 | A | 6/1998 | Southern et al. |
| 5,786,461 | A | 7/1998 | Buchardt et al. |
| 5,789,160 | A | 8/1998 | Eaton et al. |
| 5,789,162 | A | 8/1998 | Dower et al. |
| 5,789,172 | A | 8/1998 | Still et al. |
| 5,811,238 | A | 9/1998 | Stemmer et al. |
| 5,840,485 | A | 11/1998 | Lebl et al. |
| 5,843,701 | A | 12/1998 | Gold et al. |
| 5,846,839 | A | 12/1998 | Gallop et al. |
| 5,851,765 | A | 12/1998 | Koster |
| 5,858,660 | A | 1/1999 | Eaton et al. |
| 5,872,003 | A | 2/1999 | Koster |
| 5,876,693 | A | 3/1999 | Katti et al. |
| 5,888,819 | A | 3/1999 | Goelet et al. |
| 5,888,971 | A | 3/1999 | Greco et al. |
| 5,922,545 | A | 7/1999 | Mattheakis et al. |
| 5,925,517 | A | 7/1999 | Tyagi et al. |
| 5,945,325 | A | 8/1999 | Arnold et al. |
| 5,948,386 | A | 9/1999 | Katti et al. |
| 5,958,691 | A | 9/1999 | Pieken et al. |
| 5,958,703 | A | 9/1999 | Dower et al. |
| 5,980,861 | A | 11/1999 | Hnatowich et al. |
| 5,986,053 | A | 11/1999 | Ecker et al. |
| 5,998,140 | A | 12/1999 | Dervan et al. |
| 6,037,120 | A | 3/2000 | Benner |
| 6,043,031 | A | 3/2000 | Koster et al. |
| 6,048,698 | A | 4/2000 | Eaton et al. |
| 6,060,596 | A | 5/2000 | Lerner et al. |
| 6,074,823 | A | 6/2000 | Koster |
| 6,080,826 | A | 6/2000 | Grubbs et al. |
| 6,103,476 | A | 8/2000 | Tyagi et al. |
| 6,127,154 | A | 10/2000 | Mosbach et al. |
| 6,140,053 | A | 10/2000 | Koster |
| 6,140,493 | A | 10/2000 | Dower et al. |
| 6,140,496 | A | 10/2000 | Benner |
| 6,143,497 | A | 11/2000 | Dower et al. |
| 6,150,097 | A | 11/2000 | Tyagi et al. |
| 6,165,717 | A | 12/2000 | Dower et al. |
| 6,175,001 | B1 | 1/2001 | Barbas et al. |
| 6,194,144 | B1 | 2/2001 | Koster |
| 6,194,550 | B1 | 2/2001 | Gold et al. |
| 6,207,446 | B1 | 3/2001 | Szostak et al. |
| 6,214,553 | B1 | 4/2001 | Szostak et al. |
| 6,225,450 | B1 | 5/2001 | Koster |
| 6,238,871 | B1 | 5/2001 | Koster |
| 6,287,765 | B1 | 9/2001 | Cubicciotti |
| 6,291,160 | B1 | 9/2001 | Lerner et al. |
| 6,291,161 | B1 | 9/2001 | Lerner et al. |
| 6,368,874 | B1 | 4/2002 | Gallop et al. |
| 6,391,593 | B1 | 5/2002 | Weston et al. |
| 6,436,635 | B1 | 8/2002 | Fu et al. |
| 6,511,809 | B2 | 1/2003 | Baez et al. |
| 6,514,761 | B1 | 2/2003 | Reed |
| 6,607,878 | B2 | 8/2003 | Sorge |
| 6,635,235 | B1 | 10/2003 | Katti et al. |
| 6,680,192 | B1 | 1/2004 | Lerner et al. |
| 6,780,397 | B2 | 8/2004 | Katti et al. |
| 6,831,166 | B2 | 12/2004 | Manoharan et al. |
| 7,070,928 | B2 * | 7/2006 | Liu et al. ............... 435/6 |
| 7,105,308 | B2 | 9/2006 | Chan-Hui et al. |
| 7,223,545 | B2 | 5/2007 | Liu et al. |
| 7,233,545 | B2 * | 6/2007 | Harvey et al. ........... 367/127 |
| 2001/0036638 | A1 | 11/2001 | Nolan et al. |
| 2002/0034757 | A1 | 3/2002 | Cubicciotti |
| 2002/0038000 | A1 | 3/2002 | Gold et al. |
| 2002/0058242 | A1 | 5/2002 | Demers |
| 2002/0064779 | A1 | 5/2002 | Landegren et al. |
| 2002/0064798 | A1 | 5/2002 | Nolan et al. |
| 2003/0099945 | A1 | 5/2003 | Eaton et al. |
| 2003/0104389 | A1 | 6/2003 | Sergeev |
| 2003/0113738 | A1 | 6/2003 | Liu et al. |
| 2003/0143561 | A1 | 7/2003 | Pedersen et al. |
| 2004/0014090 | A1 | 1/2004 | Neri et al. |
| 2004/0049008 | A1 | 3/2004 | Pederson et al. |
| 2004/0180412 | A1 | 9/2004 | Liu et al. |
| 2004/0214902 | A1 | 10/2004 | Wang et al. |
| 2005/0009050 | A1 | 1/2005 | Nadeau et al. |
| 2005/0025766 | A1 | 2/2005 | Liu et al. |
| 2005/0042669 | A1 | 2/2005 | Liu et al. |
| 2005/0095627 | A1 | 5/2005 | Kolman et al. |
| 2005/0142583 | A1 | 6/2005 | Liu et al. |
| 2005/0170376 | A1 | 8/2005 | Liu et al. |
| 2005/0221316 | A1 * | 10/2005 | Pedersen et al. ............... 435/6 |
| 2005/0227281 | A1 | 10/2005 | Liu et al. |
| 2005/0233381 | A1 | 10/2005 | Liu et al. |
| 2005/0281819 | A9 | 12/2005 | Liu et al. |
| 2006/0121470 | A1 * | 6/2006 | Pedersen ............... 435/6 |
| 2006/0246450 | A1 * | 11/2006 | Franch et al. ............... 435/6 |
| 2007/0154899 | A1 | 7/2007 | Coull et al. |
| 2008/0318807 | A1 | 12/2008 | Liu et al. |
| 2009/0035824 | A1 | 2/2009 | Liu et al. |
| 2009/0149347 | A1 | 6/2009 | Liu et al. |
| 2009/0203530 | A1 | 8/2009 | Liu et al. |

FOREIGN PATENT DOCUMENTS

| | | |
|---|---|---|
| EP | 0 324 616 A | 7/1989 |
| EP | 0 604 552 | 2/1997 |
| EP | 0 773 227 | 5/1997 |
| EP | 0 643 778 | 5/2000 |
| WO | WO 91/05058 | 4/1991 |
| WO | WO 92/02536 | 2/1992 |
| WO | WO 93/06121 | 4/1993 |
| WO | WO 93/20242 | 10/1993 |
| WO | WO 96/09316 | 3/1996 |
| WO | WO 00/23458 | 4/2000 |
| WO | WO-00/32823 | 6/2000 |
| WO | WO 00/47775 | 8/2000 |
| WO | WO 00/61775 | 10/2000 |
| WO | WO-01/16352 | 3/2001 |
| WO | WO 02/074929 A2 | 9/2002 |
| WO | WO 02/102820 | 12/2002 |
| WO | WO 02/103008 | 12/2002 |
| WO | WO-03/031591 | 4/2003 |
| WO | WO-03/038060 | 5/2003 |
| WO | WO-03/076943 | 9/2003 |
| WO | WO-03/076944 | 9/2003 |
| WO | WO 03/078050 | 9/2003 |
| WO | WO 03/078445 | 9/2003 |
| WO | WO 03/078446 | 9/2003 |
| WO | WO 03/078625 | 9/2003 |
| WO | WO 03/078626 | 9/2003 |
| WO | WO 03/078627 | 9/2003 |
| WO | WO 03/082901 | 10/2003 |
| WO | WO 04/001042 | 12/2003 |
| WO | WO-2004/010101 | 1/2004 |
| WO | WO 2004/013070 | 2/2004 |
| WO | WO 2004/016767 | 2/2004 |
| WO | WO 2004/024929 | 3/2004 |
| WO | WO 2004/039825 | 5/2004 |
| WO | WO 2004/056994 | 7/2004 |
| WO | WO 2004/074429 | 9/2004 |
| WO | WO 2004/074501 | 9/2004 |
| WO | WO 2004/083427 | 9/2004 |
| WO | WO 2004/110964 | 12/2004 |
| WO | WO 2005/003778 | 1/2005 |
| WO | WO-2005/026387 | 3/2005 |
| WO | WO-2005/069771 | 8/2005 |
| WO | WO-2005/074417 | 8/2005 |
| WO | WO-2006/023778 | 3/2006 |
| WO | WO-2006079061 A2 | 7/2006 |
| WO | WO-2006/130669 | 12/2006 |
| WO | WO-2006/133312 | 12/2006 |
| WO | WO-2006/135654 | 12/2006 |
| WO | WO-2006/138560 | 12/2006 |
| WO | WO-2006/138666 | 12/2006 |
| WO | WO-2007/008276 | 1/2007 |

| WO | WO-2007/016488 | 2/2007 |
| --- | --- | --- |
| WO | WO-2008/036273 | 3/2008 |
| WO | WO-2008/054600 | 5/2008 |

OTHER PUBLICATIONS

Knight et al. (Clinical Chemistry, 1999, vol. 45, No. 10, p. 1860-1863).*
Calderone et al. (Agnew Chem. Int. Ed., 2002, vol. 41, No. 23, p. 4104-4108).*
Arnold et al. (1989) "Assay Formats Involving Acridinium-Ester-Labeled DNA Probes" Clin. Chem. 35(8): 1588-94.
Balachander et al. (1990) "Monolayer Transformation by Nucleophilic Substitution: Applications to the Creation of New Monolayer Assemblies," Langmuir 6(11): 1621-1627.
Bartel et al. (1993) Science 261 1411-18.
Brooker, Genetics Analysis and Principles ed. 1, 1999, Menlo Park, CA, pp. 326, 368, 372, 373, and 379.
Calderone et al. (2002) "Directing Otherwise Incompatible Reactions in a Single Solution by Using DNA-Templated Organic Synthesis," Angewandte Chemie 41(21): 4104-08.
Calderone et al. (2005) "Small-molecule diversification from iterated branching reaction pathways enabled by DNA-templated synthesis," Angewandte Chemie 44(45): 7383-86.
DeBiasi et al. (2004) "Molecular Methods for Diagnosis of Viral Encephalitis," Clinical Microbiology Reviews 17 (4): 903-925.
DeFigueiredo et al. (2004) "DARTs: A DNA-based in vitro polypeptide display technology," Proteomics 4(10): 3128-40.
Dorner et al. (1984) Journal of Virology 50(3): 507-514.
Doyon et al. (2003) "Highly Sensitive In Vitro Selections for DNA-linked synthetic small molecules with protien binding affinity and specificity," JACS 125(41): 12372-73.
Dumelin et al. (2006) "Selection of Streptavidin Binders from a DNA-Encoded Chemical Library," Amer. Chemical Soc. E-pub. Feb. 18, 2006 (5 pages).
Ekland et al. (1995) Science 269: 364-70.
European Patent Office (EPO) Examination Report; European Application No. EP 03788662.9, mailed Nov. 21, 2007 (15 pages).
Gartner et al. (2001) Supporting Materials (2 pages) for "The Generality of DNA-Templated Synthesis as a Basis for Evolving Non-Natural Small Molecules" J. Am. Chem. Soc. 123: 6961-6963 (2001).
Gartner et al. (2002) "Expanding the Reaction and Scope of DNA-Templated Synthesis," Angewandte Chemie 41(10): 1796-1800.
Gartner et al. (2002) "Multistep small-molecule synthesis programmed by DNA templates," J. Amer. Chem. Society 124(35): 10304-06.
Gartner et al. (2003) "Two-Enabling Architectures for DNA-templated Organic Synthesis," Angewandte Chemie 42(12): 1370-75.
Gartner et al. (2004) "DNA-templated organic synthesis and selection of a library of macrocycles," Science 305(5690): 1601-05.
Giulietti et al. (2001) "An overview of real-time quantitative PCR: Applications to quantify cytokine gene expression," Methods, A Companion to Methods in Enzymology 25(4): 386-401.
Goodwin et al. (1992) J. Am. Chem. Soc. 114: 9197-98.
Halpin et al. (2004) "DNA display II. Genetic manipulation of combinatorial chemistry libraries for small-molecule evolution," PLOS Biology 2(7): 1022-30.
Harris et al. (1999) "Directed Molecular Evolution," Origins of Life and Evolution of the Biosphere 29: 425-435.
Homepage of David R. Liu (http://evolve.harvard.edu) available at Mar. 11, 2000 according to the Wayback Machine (http://web.archive.org).
Homepage of David R. Liu (http://evolve.harvard.edu) available at Mar. 11, 2000 according to the Wayback Machine (http://web.archive.org).
Homepage of David R. Liu (http://evolve.harvard.edu) available at Oct. 15, 2000 according to the Wayback Machine (http://web.archive.org).
Ichida et al. (2005) "An in vitro selection system for TNA," JACS 127(9): 2802-03.
Jenne et al. (1998) Chem. Biol. 5: 23-34.
Knight et al. (1999) "Accuracy of Genotyping of Single-Nucleotide Polymorphisms by PCR-ELISA Allele-Specific Oligonucleotide Hybridization Typing and by Amplification Refractory Mutation System," Clinical Chemistry 45(10): 1860-1863.
Kuimelis et al. (1995) "Cleavage Properties of an Oligonucleotide Containing a Bridged Internucleotide 5'-Phosphothioate RNA Linkage," Nucl. Acids Res. 23(23): 4753-60.
Kurz et al. (2001) "cDNA-protein fusions: covalent protein-gene conjugates for the in vitro selection fo peptides and proteins," ChemBiochem: A European Journal of Chemical Biology 2(9): 666-72.
Laux et al. (2006) "Epidermal growth factor receptor dimerization status determines skin toxicity to HER-kinase targeted therapies," Br. J. Cancer 94(1): 85-92.
Lee et al. (2000) Nature Struct. Biol. 7: 28-33.
Ma et al. (2000) "Nucleic acid-triggered catalytic drug release," PNAS USA: 97(21): 11159-63.
Mag et al. (1991) "Synthesis and Selective Cleavage of an Oligodeoxynucleotide Containing a Bridged Internucleotide 5'-Phosphorothioate Linkage," Nucl. Acids Res.
Metelev et al. (2001) "New Chemically Reactive dsDNAs Containing Single Internucleotide Monophosphoryldithio links: reactivity of 5'-mercapto-oligodeoxyribonucleotides," Nucl. Acids Res. 29(19): 4062-69.
Opposition to European Patent No. EP1423400, filed May 9, 2007 (Communication issued from EPO on May 15, 2007).
Prabhu et al. (2000) "Unprecedented Selective Aminolysis: Aminopropyl Phosphine as a Building Block for a New Family of Air Stable Mono-, Bis-, and Tris-Primary Phosphines," JACS 122: 1554-55.
Rees et al. (2004) "Fragment-Based Lead Discovery," Nature Reviews, Drug Discovery 3(8): 660-72.
Rohatgi et al. (1996) J. Am. Chem. Soc. 118: 3332-39.
Rohatgi et al. (1996) J. Am. Chem. Soc. 118: 3340-44.
Rosenbaum et al. (2003) "Efficient and sequence-specific DNA-templated polymerization of peptide nucleic acid aldehydes," JACS 125(46): 13924-25.
Rozenman et al. (2006) "DNA-templated synthesis in organic solvents," ChemBiochem: A European Journal of Chemical Biology 7(2): 253-56.
Sakurai et al. (2005) "DNA-templated functional group transformations enable sequence-programmed synthesis using small molecule reagents," JACS 127(6) 1660-61.
Sando et al. (2002) "Quencher as leaving group: Efficient detection of DNA-joining reactions," JACS 124(10): 2096-97.
Silverman et al. (2006) "Detecting RNA and DNA with Templated Chemical Reactions," Chem. Rev. 106: 3775-89.
Snyder et al. (2005) "Ordered Multi-Step Synthesis in a Single Solution Directed by DNA Templates," Angewandte Chemie 44(45): 7379-7382.
Stains et al. (2005) "DNA Sequence-Enabled Reassembly of the Green Fluorescent Protein," JACS 127: 10782-83.
Stryer (1995) Biochemistry, 4th Edition, Chapter 37.
Suga et al. (1998) Biochem. 37: 10118-25.
Suga et al. (1998) J. Am. Chem. Soc. 120: 1151-1156.
Tamura et al. (Jul. 11, 2003) "Peptide Synthesis with a Template-like RNA guide and aminoacyl phosphate adaptors" Proc. Natl. Acad. Sci. USA 100(15): 8666-8669.
Tyagi et al. (1996) "Molecular Beacons: Probes that Fluoresce Upon Hybridization," Nature Biotechnology 14(1): 303-08.
Uttamchandani et al. (2005) "Small molecule microarrays, recent advances and applications," Curr. Opin. In Chem. Biol. 9(8): 4-13.
Xu et al. (1998) Nucl. Acids Res. 26(13): 3159-64.
Xu et al. (1999) Nucl. Acids Res. 27: 875-81.
Yang et al. (2004) "PCR-based diagnostics for infectious diseases: uses, limitations, and future applications in acute-care settings," The Lancet Infectious Diseases 4: 337-348.
Amato (1992) "Speeding Up a Chemical Game of Chance," Science 257: 330-331.
Needels et al. (1993) "Generation and screening of an oligonucleotide-encoded synthetic peptide library," PNAS 90:10700-10704.

European Patent Office (EPO) Examination Report; European Application No. 06733839.2; mailed Nov. 19, 2007; 6 pages.

Acevedo et al., "Non-Enzymatic Transcription of an Oligodeoxynucleotide 14 Residues Long" J. Mol. Biol. 197: 187-193 (1987).

Alvarez et al., "Photocleavable Protecting Groups as Nucleobase Protections Allowed the Solid-Phase Synthesis of Base-Sensitive SATE-Prooligonucleotides" J. Org. Chem. 64: 6319-6328 (1999).

Anderson et al. "A Comparison of Selected mRNA and Protein Abundances in Human Liver" Electrophiresis 18: 533-537 (1997).

Arap et al., "Steps Toward Mapping the Human Vasculature by Phage Display" Nat. Med. 8(2) 121-127 (2002).

Arnold et al., "Directed Evolution of Biocatalysts" Curr. Opin. Chem. Biol. 3: 54-59 (1999).

Arnold, "Design by Directed Evolution" Acc. Chem. Res. 31: 125-131 (1998).

Bain et al. "Ribosome-Mediated Incorporation of a Non-Standard Amino Acid into a Peptide Through Expansion of the Genetic Code" Nature 356: 537-539 (1992).

Baldwin et al. "Enzymes in Synthetic Organic Chemistry" Tetrahedron Organic Chemistry Series 12: 1-40, 1994.

Ban et al., "The Complete Atomic Structure of the Large Ribosomal Subunit at 2.4 Å Resolution" Science 289: 905-920 (2000).

Bannwarth et al., "A Simple and Effective Chemical Phosphyorylation Procedure for Biomolecules" Helv. Chim. Acta 70: 175-186 (1987).

Barbas et al., "Phage Display: A Laboratory Manual" Cold Spring Harbor Laboratory Press New York 736 pages (2001).

Barbas et al., Chem. Int. Ed. vol. 37, 1998. 2872-2875 Benner Reviews.

Becker et al., "Synthesis, Sar and In Vivo Activity of Novel Thienopyridine Sulfonamide Pyrrolidinones as Factor Za Inhibitors" Bioorg. Med. Chem. Lett. 9: 2753-2758 (1999).

Berger et al., "Universal Bases for Hybridization, Replication and Chain Termination" Nucleic Acids Research 28(15): 2911-2914 (2000).

Blanco et al., "A Method for Detecting Protein-DNA Interactions at Sites of Chromatin Replication" Analytical Biochemistry 163: 537-545 (1987).

Bogarad et al., "A Hierarchical Approach to Protein Molecular Evolution" Proc. Natl. Acad. Sci. USA 96: 2591-2595 (1999).

Böhler et al., "Template Switching Between PNA and RNA Oligonucleotides" Nature 376: 578-581 (1995).

Bolli et al., "Pyranosyl-RNA: Chiroselective Self-Assembly of Base Sequences by Ligative Oligomerization of Tetranucleotide-2'3'-Cyclophosphates (with a Commentary Concerning the Origin of Biomolecular Homochirality)" Chem. Biol. 4: 309-320 (1997).

Boschelli et al., "Synthesis of Amphotericin B. 2. Fragment C-D of the Aglycone" Tetrahedron Lett. 26: 5239-5242 (1985).

Bostwick et al., "RPR120844, A Novel, Specific Inhibitor of Coagulation Factor Xa Inhibits Venous Thrombosis in the Rabbit" Thromb Haemost 81: 157-160 (1999).

Brenner et al., "Encoded Combinatorial Chemistry" Proc. Natl. Acad. Sci. 89: 5381-5383 (1992).

Brenner et al., "In Vitro Cloning of Complex Mixtures of DNA on Microbeads: Physical Separation of Differentially Expressed cDNAs" Proc. Natl. Acad. Sci. USA 97(4): 1665-1670 (2000).

Bresler et al., "Stability of Peptidyl-tRNA—The Intermediate of Protein Synthesis" Biochimica et Biophysica Acta 155: 465-475 (1968).

Brooks et al., "Antiintegrin αv β3 Blocks Human Breast Cancer Growth and Angiogenesis in Human Skin" J. Clin. Invest. 96: 1815-1822 (1995).

Brooks et al., "Disruption of Angiogenesis by PEX, a Noncatalytic Metalloproteinase Fragment with Integrin Binding Activity" Cell 92: 391-400 (1998).

Brooks et al., Integrin αv β3 Antagonists Promote Tumor Regression by Inducing Apoptosis of Angiogenic Blood Vessels Cell 79: 1157-1164 (1994).

Bruick et al., "Template-Directed Ligation of Peptides to Oligonucleotides" Chem. Biol. 3: 49-56 (1996).

Cadwell et al., "Randomization of Genes by PCR Mutagenesis" PCR Methods Appl. 2: 28-33 (1992).

Celewicz et al., "Mass Spectrometry of Some Derivatives of 5-(Indol-2-yl) Pyrimidine" Pol. J. Chem. 72: 725-734 (1998).

Chan et al., "Intra-tRNA distance measurements for nucleocapsid protein-dependent tRNA unwinding during priming of HIV reverse transcription" Proc. Natl. Acad. Sci. USA 96: 459-464 (1999).

Chen et al., "Template-Directed Synthesis on Oligodeoxycytidylate and Polydeoxycytidylate Templates" J. Mol. Biol. 181: 271-279 (1985).

Cho et al., "An Unnatural Biopolymer" Science 261: 1303-1305 (1993).

Choi et al., "Inhibition of Neointimal Hyperplasia by Blocking a?β3 Integrin with a Small Peptide Antagonist Gpen GRGDSPCA" J. Vasc. Surg. 19: 125-134 (1994).

Choi-Sledeski et al., "Sulfonamidopyrrolidinone Factor Xa Inhibitors: Potency and Selectivity Enhancements via P-1 and P-4 Optimization" J. Med. Chem. 42: 3572-3587 (1999).

Collado et al., "Diastereoselective Functionalization of 5-Hydroxy Prolinates by Tandem Horner-Emmons-Michael Reaction" Tetrahedron Lett. 35: 8037 (1994).

Compton, "Nucleic Acid Sequence-Based Amplification" Nature 350: 91-92 (1991).

Czlapinski et al., "Nucleic Acid Template-Directed Assembly of Metallosalen-DNA Conjugates" J. Am. Chem. Soc. 123: 8618-8619 (2001).

Davis, "Intermediates in Amino Acid Biosynthesis" Adv. Enzymol. 16: 287-295 (1955).

Dechantsreiter et al., "N-Methylated Cyclic RGD Peptides as Highly Active and Selective αv β3 Integrin Antogaonists" J. Med. Chem. 42: 3033-3040 (1999).

Dewey et al., "New Uridine Derivatives for Systematic Evolution of RNA Ligands b Exponential Enrichment" J. Am. Chem. Soc. 117: 8474-8475 (1995).

Dietz et al., Photochemical Reduction of 5-Bromouracil by Cystine Derivatives and Coupling of 5-Bromouracil to Cystine Derivatives: Photochemistry and Photobiology 49(2): 121-129 (1989).

Drews, "Drug Discovery: A Historical Perspective" Science 287: 1960-1964 (2000).

Eaton, "The Joys of In Vitro Selection: Chemically Dressing Oligonucleotides to Satiate Protein Targets" Current Opinion in Chemical Biology 1: 10-16 (1997).

El-Dorry, "Purification of mRNA Coding for Rat-Liver Fructose-1,6-bisphosphatase by polysome immunoabsorption" Biochimica et Biophysica Acta 867: 252-255 (1986).

Eliseev et al., "Dynamic Combinatorial Chemistry: Evolutionary Formation and Screening of Molecular Libraries" Combinatorial Chemistry in Biology 243: 159-172 (1999).

Ellis et al., "Functional Analysis of the T-Cell Restricted Protein Tyrosine Kinase TxK" Biochem. J. 335: 277-284 (1998).

Ewing et al., "Design and Structure—Activity Relationships of Potent and Selective Inhibitors of Blood Coagulation Factor Xa" J. Med. Chem. 42: 3557-3571 (1999).

Famulok et al., "Oligonucleotide Libraries-Variatio Delectat" Curr. Opin. Chem. Biol. 2: 320-327 (1998).

Fenn et al., "Direct Quantitation of Biotin-Labeled Nucleotide Analogs in RNA Transcripts" Analytical Chemistry 190: 78-83 (1990).

Fleet et al., "Enantiospecific Synthesis of Shikimic Acid from D-Mannose: Formation of a Chiral Cyclohexene by Intramolecular Olefination of a Carbohydrate-Derived Intermediate" J. Chem. Soc. Perkins, Trans. I: 905-908 (1984).

Fleischer et al., "Conversion of Aliphatic and Alicyclic Polyalcohols to the Corresponding Primary Polyamine" J. Org. Chem. 36(20): 3042-3044 (1971).

Francis et al., "Combinatorial Libraries of Transition-Metal Complexes, Catalysts and Materials" Curr. Opin. Chem. Biol. 2: 422-428 (1998).

Francis et al., "Discovery of Novel Catalysts for Alkene Epoxidation from Metal-Binding Combinatorial Libraries" Angew. Chem. Int. Ed. Engl. 38: 937-941 (1999).

Frankel et al., "Encodamers: Unnatural Peptide Oligomers Encoded in RNA" Chemistry and Biology 10: 1043-1050 (2003).

Friedlander et al., "Definition of Two Angiogenic Pathways by Distinct aυ Integrins" Science 270: 1500-1502 (1995).

Fruchart et al., "A New Linker for the Synthesis of C-Terminal Peptide α-oxo-Aldehydes" Tetrahedron Lett. 40: 6225 (1999).
Fruchtel et al., "Organic Chemistry on Solid Supports" Angew. Chem. Int. Ed. Engl. 35: 17-42 (1996).
Gad, "Synaptic Vesicle endocytosis studied in a living synapse" Nobel Institute for Neurophysiology, Karolinska Institutet, Sweden 1-48 (2000).
Gallop et al., "Applications of Combinatorial Technologies to Drug Discovery, 1. Background and Peptide Combinatorial Libraries" J. Med. Chem. 37: 1233-1251 (1994).
Gartner et al., "The Generality of DNA-Templated Synthesis as a Basis for Evolving Non-Natural Small Molecules" J. Am. Chem. Soc. 123: 6961-6963 (2001).
Gat et al., "Reading DNA Differently" Biopolymers 48: 19-28 (1998).
Gevorkian et al. "Rapid Communication Identification of Autoimmune Thrombocytopenic Purpura-Related Epitopes using Phage-Display Peptide Library" Clin. Immunol. Immunopathol 86: 305-309 (1998).
Geyer et al., "Conformational Analysis of a Cyclic RGD Peptide Containing a Ψ [CH2-NH] Bond: A Positional Shift in Backbone Structure Caused by a Single Dipeptide Mimetic" J. Am. Chem. Soc. 116: 7735-7743 (1994).
Gilbertson et al., "Asymmetric Catalysis with Libraries of Palladium β-Turn Phosphine Complexes" J. Am. Chem. Soc. 122: 6522-6523 (2000).
Gocke, "Mechanism of Quinolone Mutagenicity in Bacteria" Mutation Research 248: 135-143 (1991).
Gordon et al., Applications of Combinatorial Technologies to Drug Discovery. 2. Combinatorial Organic Synthesis, Library Screening Strategies, and Future Directions, J. Med. Chem. 37(10): 1385-1401 (1994).
Gourlain et al., "Enhancing the Catalytic Repertoire of Nucleic Acids. II. Simultaneous Incorporation of Amino and Imidazolyl Functionalities by Two Modified Triphosphates During PCR" Nucleic Acids Res. 29: 1898-1905 (2001).
Greene et al., "Protective Groups in Organic Synthesis 3rd ed.", 780 pages Wiley & Sons (1999).
Grubina et al., "Summer Research Report: DNA-Templated Synthesis of a Synthetic Small Molecule Library" The Nucleus Jan. 10-14, 2004.
Gryaznov et al., "Chemical Ligation of Oligonucleotides in the Presence and Absence of a Template" J. Am. Chem. Soc. 115: 3808-3809 (1993).
Gryaznov et al., "Template Controlled Coupling and Recombination of Oligonucleotide Blocks Containing Thiophosphoryl Groups" Nucleic Acids Research 21(6): 1403-1408 (1993).
Guatelli et al., "Isothermal, In Vitro Amplification of Nucleic Acids by a Multienzyme Reaction Modeled After Retroviral Replication" Proc. Natl. Acad. Sci. 87: 1874-1878 (1990).
Gyllensten et al., "Generation of Single-Stranded DNA by the Polymerase Chain Reaction and its Application to Direct Sequencing of the HLA-DQA locus", PNAS 85: 7652-7656 (1988).
Haaima et al., "Peptide Nucleic Acids (PNAs) Containing Thymine Monomers Derived from Chiral Amino Acids: Hybridization and Solubility Properties of D-Lysine PNA" Angew. Chem. Int. Ed. Engl. 35: 1939-1942 (1996).
Haeuptle et al., "Translation Arrest by Oligodeoxynucleotides Complementary to mRNA Coding Sequences Yields Polypeptides of Predetermined Length" Nucleic Acids Research 14(3): 1427-1448 (1986).
Hamburger et al., "Peptidyl-tRNA XI. The Chemical Synthesis of Phenylalanine-Containing Oligopeptidyl-tRNA" Biochimica et Biophysica Acta, 213: 115-123 (1970).
Haubner et al. "Structural and Functional Aspects of RGD-Containing Cyclic Pentapeptides as Highly Potent and Selective Integrin αv β3 Antagonists" J. Am. Chem. Soc. 118: 7461-7472 (1996).
Herrera-Estrella et al., "VirD Proteins of *Agrobacterium tumefaciens* are Required for the Formation of a Covalent DNA—Protein Complex at the 5' Terminus of T-Strand Molecules" The EMBO Journal 7(13): 4055-4062 (1988).

Herrlein et al., "A Covalent Lock for Self-Assembled Oligonucleotide Conjugates" J. Am. Chem. Soc. 117: 10151-10152 (1995).
Heywood et al., "A Study of Muscle Polyribosomes and the Coprecipitation of Polyribosomes with Myosin" J. Biol. Chem. 7: 3289-3296 (1968).
Heywood et al., "The Identification of Polyribosomes Synthesizing Myosin" PNAS 57: 1002-1009 (1967).
Hirama et al., "Asymmetric Induction in the Intramolecular Conjugate Addition of − or δ- Carbamoyloxy - , β-Unsaturated Esters. A New Method for Diastereoselective Amination and Divergent Synthesis of 3-Amino-2,3,6-Trideoxyhexoses" Heterocycles 28: 1229-1247 (1989).
Hirama et al., "Intramolecular Michael Addition of O-Carbamates to α,β Unsaturated Esters: A New Diastereoselective Amination in an Acyclic System" J. Am. Chem. Soc. 107: 1797-1798 (1985).
Hooper et al., "Mode of Action of the New Quinolones: New Data" Eur. J. Clin. Microbiol. Infect. Dis. 10(4): 223-231 (1991).
Houdebine et al., "Purification of the mRNAs for Ewe αs -Casein and β-Casein by Immunoprecipitation of of Polysomes" Eur. J. Biochem. 63: 9-14 (1976).
House et al., "The Chemistry of Carbanions. XVII. The Addition of Methyl Organometallic Reagents to Cyclohexenone Derivatives" J. Org. Chem. 33: 949 (1968).
Hughes, "Application of Polymer-Bound Phosphonium Salts as Traceless Supports for Solid" Tetrahedron Lett. 37: 7595-7598 (1996).
Hyrup et al., "Peptide Nucleic Acids (PNA): Synthesis, Properties and Potential Applications" Bioorganic & Medical Chemistry 4(1): 5-23 (1996).
Illuminati et al., "Ring Closure Reactions of Bifunctional Chain Molecules" Acc. Chem. Res. 14: 95-102 (1981).
Inoue et al., "Oligomerization of (Guanosine 5' -Phosphor)-2-Methylimidazolide on Poly(C): An RNA Polymerase Model" J.Mol. Biol. 162: 201-217 (1982).
Inoue et al., "Substituent Control of the Poly(C)—Directed Oligomerization of Guanosine 5'—Phosphoroimidazolide" J. Am. Chem. Soc. 103: 7666-7667 (1981).
Inoue et al., "Template-Directed Synthesis on the Pentanucleotide CpCpGpCpC" J. Mol. Biol. 178: 669-676 (1984).
International Search Report for Application No. PCT/US02/08546 dated Dec. 17, 2002.
International Search Report for Application No. PCT/US03/25984 dated Jan. 18, 2005.
Ito et al., "Acetone-Sensitized Photocoupling of 5-Bromouridine to Trytophan Derivatives via Electron-Transfer Process" J. Amer. Chem. Soc. 102: 7535-7541 (1980).
Jemth et al., "Kinetic Characterization of Recombinant Human Glutathione Transferase T1-1, A Polymorphic Detoxication Enzyme" Arch. Biochem. Biophys. 348(2): 247-54 (1997).
Johansson et al., "Regioselctive Reductive Ring-Opening of 4-Methoxybenzylidene Acetals of Hexopyranosides. Access to a Novel Protecting-Group Strategy. Part 1" J. Chem. Soc. Perkins Trans. I: 2371-2374 (1984).
Johnson et al. "Evidence for Posttranslational O-Glycosylation of Fetuin" Biochemistry 25: 5518-5525 (1986).
Johnston et al., "RNA-Catalyzed RNA Polymerization: Accurate and General RNA-Templated Primer Extension" Science 292: 1319-1325 (2001).
Jost et al., "Quantitative Precipitation of Short Oligonucleotides with Low Concentrations of Cetyltrimethylammonium Bromide" Nucleic Acids Res. 17: 2143 (1989).
Kahl et al., "Introducing Structural Diversity in Oligonucleotides via Photolabile, Convertible C5-Substituted Nucleotides" J.Am. Chem. Soc. 121(4): 597-604 (1999).
Keiler et al., "Role of a Peptide Tagging System in Degradation of Proteins Synthesized from Damaged Messenger RNA" Science 271: 990-993 (1996).
King et al., Bis (Dialkylamino) Phosphines J. Org. Chem. 49: 1784-1789 (1984).
Kinoshita et al., "Enzymatic Synthesis of Code Regions for Encoded combinatorial Chemistry (ECC)" Nucleic Acids Symposium Series 34: 201-202 (1995).

Kuntz et al., "Combinatorial Catalyst Discovery" Current Opinion in Chemical Biology 3: 313-319 (1999).

Kupsch et al., "Isolation of Human Tumor-Specific Antibodies by Selection of an Antibody Phage Library on Melanoma Cells" Clin Cancer Res. 5: 925-931 (1999).

Latham et al. "The Application of a Modified Nucleotide in Aptamer Selection: Novel Thrombin Aptamers Containing 5-(Pentynyl)-2'—Deoxyuridine" Nucleic Acids Res. 22: 2817-2822 (1994).

Leadley et al., "Pharmacodynamic Activity and Antithrombotic Efficacy of RPR120844, a Novel Inhibitor of Coagulation Factor Xa" J. Cardiovasc. Pharmacol. 34: 791-799 (1999).

Lee et al., "Enhancing the Catalytic Repertoire of Nucleic Acids: a Systematic Study of Linker Length and Rigidity" Nucleic Acids Res. 29: 1565-1573 (2001).

Leon et al., "Covalent Coupling of 4-Thiouridine in the Initiator Methionine tRNA to Specific Lysine Residues in *Escherichia coli* Methionyl-tRNA Synthetase" Biochemistry 26: 7113-7121 (1987).

Li et al. "DNA-Catalyzed Polymerization" J. Am. Chem. Soc. 124: 746-747 (2002).

Li et al., "A Catalytic DNA for Porphyrin Metallation" Nat. Struct. Biol. 3: 743-747 (1996).

Li et al., "Capping DNA with DNA" Biochemistry 39: 3106-3114 (2000).

Li et al., "Chemical Self-Replication of Palindromic Duplex DNA" Nature 369: 218-221 (1994).

Li et al., "Phosphorylating DNA with DNA" Proc. Natl. Acad. Sci. USA 96: 2746-2751 (1999).

Li et al., "Toward an Efficient DNAzyme" Biochemistry 36: 5589-5599 (1997).

Lin et al. "Formation of an Amino-Acid-Binding Pocket Through Adaptive Zippering-Up of a Large DNA Hairpin Loop" Chem. Biol. 5: 555-572 (1998).

Lin et al., "Structural Basis of DNA Folding and Recognition in an AMP-DNA Aptamer Complex: Distinct Architectures But Common Recognition Motifs for DNA and RNA Aptamers Complexed to AMP" Chem. Biol. 4: 817-832 (1997).

Liu et al. "Generating New Molecular Function: A Lesson from Nature" Angew. Chem. Intl. Ed. Eng. 38: 37-54 (1999).

Loss, "Spin-based Quantum Information Processing in Nanostructures" Dept. of Phys., Univ. of Basel, Switzerland, May 29-31, 2002.

Luo et al., "Analysis of the Structure and Stability of a Backbone-Modified Oligonucleotide: Implications for Avoiding Product Inhibition in Catalytic Template-Directed Synthesis" J. Am. Chem. Soc. vol. 120, No. 13: 3019-3031 (1998), see entire document, especially pp. 3019-3020.

Luther et al., "Surface-Promoted Replication and Exponential Amplification of DNA Analogues" Nature 396: 245-248 (1998).

Lynn et al., "Water-Soluble Ruthenium Alkylidenes: Synthesis, Characterization, and Application to Olefin Metathesis in Protic Solvents" J. Am. Chem. Soc. 122: 6601-6609 (2000).

Lynn et al., Living Ring-Opening Metathesis Polymerization in Water J. Am. Chem. Soc. 12: 1627-1628 (1998).

MacLean et al., "Encoded Combinatorial Chemistry Synthesis and Screening of a Library of Highly Functionalized Pyrrolidines" Proc. Natl. Acad. Sci. USA 94: 2805-2810 (1997).

Magid, "Nucleophilic and Organometallic Displacement Reactions of Allylic Compounds: Stereo- and Regiochemistry" Tetrahedron 36: 1901-1930 (1980).

Mahal et al., "Engineering Chemical Reactivity on Cell Surfaces Through Oligosaccharid Biosynthesis" Science 276: 1125-1128 (1997).

Maignan et al., "Crystal Structures of Human FactorXa Complexed with Potent Inhibitors" J. Med. Chem. 43: 3226-3232 (2000).

Marks et al., "Molecular Evolution of Proteins on Filamentous Phage" J. Biol. Chem. 267(23): 16007-16010 (1992).

Marlowe et al., "Design, Synthesis and Structure-Activity Relationship of a Series of Arginine Aldehyde Factor Xa Inhibitors. Part 1: Structures Based on the (D)-Arg-Gly-Arg Tripeptide Sequence" Bioorg. Med. Chem. Lett. 10: 13-16 (2000).

Mattheakis et al., "An In Vitro Polysome Display System for Identifying Ligands from Very Large Peptide Libraries" Proc. Natl. Acad. Sci. USA 91: 9022-9026 (1994).

Mel'nikov et al., "Solubilization of DNA-Cationic Lipid Complexes in Hydrophobic Solvents. A Single-Molecule Visualization by Fluorescence Microscopy" Langmuir 15: 1923-1928 (1999).

Minshull et al., "Protein Evolution by Molecular Breeding" Curr. Opin. Chem. Biol. 3: 284-290 (1999).

Mirza et al., "Synthesis of Shikimic Acid and Its Phosphonate Analogue Via Knoevenagel Condensation" Tetrahedron Lett. 32: No. 33, 4111-4114 (1991).

Miyamoto-Sato et al., "Highly stable and efficient mRNA templates for mRNA-protein fusions and C-terminally labeled proteins" Nucleic Acids Research vol. 31 No. 15 e78 (2003).

Mohr et al., "Synthesis of Water-Soluble, Aliphatic Phoshines and Their Application to Well-Defined Ruthenium Olefin Metathesis Catalysts" Organometallics 15: 4317-4325 (1996).

Muth et al., "A Single Adenosine with a Neutral pKa in the Ribosomal Peptidyl Transferase Center" Science 289: 947-950 (2000).

Nagasaka et al., "Wittig Reactions of 1-Alkoxycarbonyl-2-Hydroxypyrrolidines and—Piperidines: Synthesis of (±)—Hygrine and ((±)-2-Epilasubine II" Heterocycles 29: 155-164 (1989).

Nakano et al., "General Acid-Base Catalysis in the Mechanism of a Hepatitis Delta Virus Ribozyme" Science 287: 1493-1497 (2000).

Nazarenko et al., "A closed tube format for amplification and detection of DNA based on energy transfer" Nucleic Acid Research 25(12): 2516-2521 (1997).

Nemoto et al., "In vitro virus: Bonding of mRNA bearing puromycin at the 3'-terminal end to the C-terminal end of its encoded protein on the ribosome in vitro" European Biochemical Societies Letters 414: 405-408 (1997).

Nissen et al., "The Structural Basis of Ribosome Activity in Peptide Bond Synthesis" Science 289: 920-930 (2000).

Nolte et al., "Mirror-Design of L-Oligonucleotide Ligands Binding to L-Arginine" Nature Biotechnology 14: 1116-1121 (1996).

Norris et al., "Mechanistic Studies of the 5-Iodouracil Chromophore Relevant to Its Use in Nucleoprotein Photo-Cross-Linking" J. Amer. Chem. Soc. 118: 5796-5803 (1996).

Olofson et al., "Selective N-Dealkylation of Teritiary Amines with Vinyl Chloroformate: An Improved Synthesis of Naloxone" Tetrahedron Lett. 18: 1567-1570 (1977).

Olofson et al., "Use of the Vinyloxycarbonyl Group for Amino Protection in Peptide Synthesis" Tetrahedron Lett. 18: 1563-1566 (1977).

Olofson et al., "Value of Vinyloxycarbonyl Unit in Hydroxyl Protection: Application to the Synthesis of Nalorphine" Tetrahedron Lett. 18: 1571-1574 (1977).

Orgel et al., "Unnatural Selection in Chemical Systems" Acc. Chem. Res. 28: 109-118 (1995).

Pagratis et al., "Potent 2'-Amino-, and 2'-Fluoro-2'—Deoxyribonucleotide RNA Inhibitors of Keratinocyte Growth Factor" Nature Biotechnology 15: 68-72 (1997).

Pasqualini et al., "Aminopeptidase N Is a Receptor for Tumor-homing Peptides and a Target for Inhibiting Angiogenesis" Cancer Res. 60: 722-727 (2000).

Pasqualini et al., "Organ Targeting In Vivo Using Phage Display Peptide Libraries" Nature 380: 364-366 (1996).

Pedersen et al., "A Method for Directed Evolution and Functional Cloning of Enzymes" Proc. Natl. Acad. Sci. USA 95: 10523-10528 (1998).

Perrin et al., "Bridging the Gap Between Protein and Nucleic Acids: A Metal-Independent RNAseA Mimic with Two Protein-Like Functionalities" J. Am. Chem. Soc. 123: 1556-1563 (2001).

Perrin et al., "Expanding the Catalytic Repertoire of Nucleic Acid Catalysts: Simultaneous Incorporatio of Two Modified Deoxyribonucleoside Triphosphates Bearing Ammonium and Imidazolyl Functionalities" Nucleosides & Nucleotides 18: 377-391 (1999).

Pfaff et al., "Selective Recognition of Cyclic RGD Peptides of NMR Defined Conformation of αIIbβ3, α5β1 Integrins" J. Biol. Chem. 269: 20233-20238 (1994).

Polacek et al., "Ribosomal Peptidyl Transferase can Withstand Mutations at the Putative Catalytic Nucleotide" Nature 411: 498-501 (2001).

Püschl et al., "Peptide Nucleic Acids (PNAs) with a Functional Backbone" Tetrahedron Lett. 39: 4707-4710 (1998).

Rai et al., "Development of Potent and Selective Factor Xa Inhibitors" Bioorg. Med. Chem. Lett. 11: 1797-1800 (2001).
Rembold et al., "Single-Strand Regions of Poly(G) Act as Templates for Oligo(C) Synthesis" J. Mol. Evol. 38: 205-210 (1994).
Roberts et al., "RNA-Peptide Fusions for the In Vitro Selection of Peptides and Proteins" Proc. Natl. Acad. Sci. USA 94: 12297-12302 (1997).
Rodriguez et al., "Template-Directed Extension of a Guanosine 5'-Phosphate Covalently Attached to an Oligodeoxycytidylate Template" J. Mol. Evol. 33: 477-482 (1991).
Saiki et al., "Enzymatic Amplification of β-Globin Genomic Sequences and Restriction Site Analysis for Diagnosis of Sickle Cell Anemia" Science 230: 1350-1354 (1985).
Sakthivel et al., "Expanding the Potential of DNA for Binding and Catalysis: Highly Functionalized dUTP Derivatives That Are Substrates for Thermostable DNA Polymerases" Angew. Chem. Int. Ed. 37: 2872-2875 (1998).
Salas et al., "Biosynthetic Polydeoxynucleotides as Direct Templates for Polypeptide Synthesis" Journal of Biological Chemistry 243(5): 1012-1015 (1968).
Santoro et al., "A General Purpose RNA-Cleaving DNA Enzyme" Proc. Natl. Acad. Sci. USA 94: 4262-4266 (1997).
Saxon et al., "A 'Traceless' Staudinger Ligation for the Chemoselective Synthesis of Amide Bonds" Organic Letters 2(14): 2141-2143 (2000).
Scharf et al., "Direct Cloning and Sequence Analysis of Enzymatically Amplified Genomic Sequences" Science 233: 1076-1078 (1986).
Scheffer et al., "Selection and Characterisation of a Phage-Displayed Human Antibody (Fab) Reactive to the Lung Resistance-Related Major Vault Protein" Br. J. Cancer 86: 954-962 (2002).
Schmidt et al., "Information Transfer from DNA to Peptide Nucleic Acids by Template-Directed Syntheses" Nucleic Acids Res. 25: 4792-4796 (1997).
Schmidt-Dannert et al., "Directed Evolution of Industrial Enzymes" Trends Biotechnol. 17: 135-136 (1999).
Scholl et al., "Synthesis and Activity of a New Generation of Ruthenium-Based Olefin Metathesis Catalysts Coordinated with 1,3-Dimesityl-4,5-Dihydroimidazol-2-Ylidene Ligands" Org. Lett. 1(6): 953-956 (1999).
Schultze et al., Three-Dimensional Solution Structure of the Thrombin-Binding DNA Aptamer d(GGTTGGTGTGGTTGG) J. Mol. Biol. 235: 1532-1547 (1994).
Schwartz et al., "Template-Directed Synthesis of Novel, Nucleic Acid-Like Structures" Science 228: 585-587 (1985).
Scott, "How Were Porphyrins and Lipids Synthesized in the RNA World?" Tetrahedron Lett. 38: 4961-4964 (1997).
Seeberger et al., "Solid-Phase Oligosaccharide Synthesis and Combinatorial Carbohydrate Libraries" Chem. Rev. 100: 4349-4393 (2000).
Seeberger, P.H., Ed., "Solid Support Oligosaccharide Synthesis and Combinatorial Carbohydrate Libraries" Wiley-Interscience: New York 2001.
Seela et al., "Oligonucleotides Containing 7-Deazaadenines: The Influence of the 7-Substituent Chain Length and Charge on the Duplex Stability" Helv. Chem. Acta. 82: 1878-1898 (1999).
Seela et al., "Palladium-Catalyzed Cross Coupling of 7-Iodo-2' Deoxytubercidin with Terminal Alkynes" Synthesis: 726-730 (1996).
Shao et al., "Random-Priming in Vitro Recombination: An Effective Tool for Directed Evolution" Nucleic Acids Research 26(2): 681-83 (1998).
Sheppard et al., "A DNA Enzyme with N-Glycosylase Activity" Proc. Natl. Acad. Sci. USA 97: 7802-7807 (2000).
Shimizu et al., "Search for Chiral Catalysts Through Ligand Diversity: Substrate-Specific Catalysts and Ligand Screening on Solid Phase" Angew. Chem. Int. Ed. 36(16): 1704-1707 (1997).
Shishido et al., "1,2-Asymmetric Induction in Intramolecular Michael Reaction. A Novel and Enantioselective Route to (+) Geissman Lactone" J. Chem. Soc. Perkins Trans. I: 993-1004 (1987).
Siegel et al., "Isolation of Cell Surface-Specific Human Monoclonal Antibodies Using Phage Display and Magnetically-Activated Cell Sorting: Applications in Immunohematology" J. Immunol. Methods 206: 73-85 (1997).
Smith, G., "Filamentous Fusion Phage: Novel Expression Vectors That Display Cloned Antigens on the Virion Surface" Science 228: 1315-1317 (1985).
Smith, G., "The Progeny of Sexual PCR" Nature 370: 324-325 (1995).
Soumillion et al., "Selection of β-Lactamase on Filamentous Bacteriophage by Catalytic Activity" J. Mol. Biol. 237: 415-22 (1994).
Stemmer et al., "DNA Shuffling by Random Fragmentation and Reassembly: In Vitro Recombination for Molecular Evolution" Proc. Natl. Acad. Sci. USA 91: 10747-10751 (1994).
Stemmer, "Rapid Evolution of a Protein In Vitro by DNA Shuffling" Nature 370: 389-391 (1994).
Still et al., "Chemical Consequences of Conformation in Macrocyclic Compounds," Tetrahedron 37: 3981-3996 (1981).
Summerer D. et al., "DNA-Templated Synthesis: More Versatile Than Expected" Angewandte Chemie. Int'l Edit., Verlag Chemie. Weinheim, DE, vol. 41, No. 1: 89-90 (2002).
Supplementary European Search Report for Application No. EP 02 75 3671 dated Sep. 21, 2004.
Sutherlin et al., "Stereoselective Synthesis of Dipyranyl C-Disaccharides" Tetrahedron Lett. 34(31): 4897-4900 (1993).
Tamura et al., "Oligonucleotide-Directed Peptide Synthesis in a Ribosome- and Ribozyme-Free System" Proc. Natl. Acad. Sci. USA 98: 1393-1397 (2001).
Tarasow et al., "Dressed for Success: Realizing the Catalytic Potential of RNA" Biopolymers 48: 29-37 (1998).
Tseng-Law et al., "Identification of a Peptide Directed Against the Anti-CD34 Antibody, 9C5, by Phage Display and Its Use in Hematopoietic Stem Cell Selection" Exp. Hematol 27: 936-945 (1999).
Uhlmann et al., "Synthesis and Properties of PNA/DNA Chimeras" Angew. Chem. Int. Ed. Engl. 35: 2632-2635 (1996).
Vacca et al., "New Advances in the Discovery of Thrombin and Factor Xa Inhibitors" Curr. Opin. Chem. Biol. 4: 394-400 (2000).
Van Gelder et al., PNAS, 85: 77652-77656 (1988) Could not identify this cite. But found what might be the correct article: Van Gelder et al., "Amplified RNA Synthesized from Limited Quantities of Heterogenous cDNA," PNAS, 87: 1663-1667 (1990).
Varner et al., "Review: αv β3: The Integrin Angiogenesis and Apoptosis" Cell Adhes Commun 3: 367-374 (1995).
Visscher et al., "Template-Directed Synthesis of Acyclic Oligonucleotide Analogs" Journal of Molecular Evolution 28: 3-6 (1988).
Walder et al., "Complementary Carrier Peptide Synthesis: General Strategy and Implications for Prebiotic Origin of Peptide Synthesis" Proc. Nat. Acad. Sci. USA 76(1): 51-55 (1979).
Wells et al., "Rapid Evolution of Peptide and Protein Binding Properties in Vitro" Curr. Opin. Struct. Biol. 2: 597-604 (1992).
Wermuth et al., "Stereoisomerism and Biological Activity of the Selective and Superactive αv β3 Integrin Inhibitor Cyclo (-RGDfV-) and Its Retro-Inverso Peptide" J. Am. Chem. Soc. 119: 1328-1335 (1997).
Wiegand et al., "Selection of RNA Amide Synthases" Chemistry and Biology 4: 675-683 (1997).
Wilson et al., "In Vitro Selection of Functional Nucleic Acids" Annu. Rev. Biochem. 68: 611-647 (1999).
Winter et al., "Making Antibodies by Phage Display Technology" Annu. Rev. Immunol. 12: 433-455 (1994).
Wong et al., "Enzymes in Synthetic Organic Chemistry" 388 pages Pergamon: Tetrahedron Organic Chemistry Series 12: 1994 (Index only enclosed).
Woodward et al., "Asymmetric Total Synthesis of Erythromycin. 1. Synthesis of an Erythronolide A Seco Acid Derivative via Asymmetric Induction" J. Am. Chem. Soc. 103: 3210-3213 (1981).
Xu et al., "Nonenzymatic Autoligation in Direct Three-Color Detection of RNA and DNA Point Mutations" Nature Biotechnology 19: 148-152 (2001).

Xu et al., "Rapid and Selective Selenium-Mediated Autoligation of DNA Strands" J. Am. Chem. Soc. 122: 9040-9041 (2000).

Zarling et al., "Mapping of Lymphocyte Surface Polypeptide Antigens by Chemical Cross-Linking with Bsocoes" J. Immunology 124: 913-920 (1980).

Zhan et al. "Chemical Amplification through Template-Directed Synthesis" J. Am. Chem. Soc. vol. 119, No. 50: 12420-12421 (1997), see entire document.

Zhang et al., "Lactone and Lactam Library Synthesis by Silver Ion-Assisted Orthogonal Cyclization of Unprotected Peptides" J. Am. Chem. Soc. 121: 3311-3320 (1999).

Zhao et al., "A Methodological Comparison: The Advantage of Phosphorimidates in Expanding the Sugar Nucleotide Repertoire" J. Org. Chem. 63: 7568-7572 (1998).

Zhao et al., "Molecular Evolution by Staggered Extension Process (StEP) in Vitro Recombination" Nature Biotechnology 16(3): 258-61 (1998).

Zhao et al., "Optimization of DNA Shuffling for High Fidelity Recombination" Nucleic Acids Research 25(6): 1307-1308 (1997).

Schmidt et al., "Information Transfer from Peptide Nucleic Acids to RNA by Template-Directed Syntheses" Nucleic Acids Research 25(23): 4797-4802 (1997).

Dewey et al., "Integrated drug discovery technology in a test tube," www.currentdrugdiscovery.com (Jul. 2002).

Kanavarioti et al., Journal of Organic Chemistry vol. 64, pp. 8323-8333 (Oct. 1999).

Letter from Mr. Iver P. Cooper to the Office of Naval Research, dated May 25, 2004.

Letter from the Office of Naval Research to Mr. Iver P. Cooper, dated Feb. 1, 2005.

Appeal letter and memorandum to the General Counsel of the Navy on behalf of Mr. Iver P. Cooper, dated Apr. 1, 2005.

Letter from the Office of the General Counsel of the Navy to Mr. Iver P. Cooper, dated Aug. 5, 2005.

Slides 1, 2, 3, and 30 of Professor David Liu's slide presentation entitled "Unnatural Molecule Evolution.", Nov. 2000.

Plaintiffs Complaint, filed Nov. 18, 2005, *Iver P. Cooper v. U.S. Department of Navy*, Case 1:05-cv-02252-EGS.

Defendant's Answer to Plaintiffs Complaint, filed Feb. 10, 2006, *Iver P. Cooper v. U.S. Department of Navy*, Case 1:05-cv-02252-EGS.

Motion of Plaintiff Iver Cooper for Summary Judgment, filed May 15, 2006, *Iver P. Cooper v. U.S. Department of Navy*, Case 1:05-cv-02252-EGS.

Plaintiff's Memorandum of Points & Authorities of Plantiff Iver Cooper in Support of his Motion for Summary Judgment, filed May 15, 2006, *Iver P. Cooper v. U.S. Department of Navy*, Case 1:05-cv-02252-EGS.

Defendant's Motion for Summary Judgment, filed May 15, 2006, *Iver P. Cooper v. U.S. Department of Navy*, Case 1:05-cv-02252-EGS.

Defendant's Memorandum of Law in Support of Defendant's Motion for Summary Judgment, filed May 15, 2006, *Iver P. Cooper v. U.S. Department of Navy*, Case 1:05-cv-02252-EGS.

Defendant's Opposition to Plaintiffs Cross Motion for Summary Judgment, filed Jun. 21, 2006, *Iver P. Cooper v. U.S. Department of Navy*, Case 1:05-cv-02252-EGS.

Plaintiff's Memorandum of Points & Authorities of Plantiff Iver Cooper in Opposition to Defendant's Motion for Summary Judgment, filed Jun. 21, 2006, *Iver P. Cooper v. U.S. Department of Navy*, Case 1:05-cv-02252-EGS.

Defendant's Reply to Plaintiffs Opposition to Defendant's Motion for Summary Judgment, *Iver P. Cooper v. U.S. Department of Navy*, Case 1:05-cv-02252-EGS, Jul. 20, 2006.

Plaintiff's Reply in Support of His Motion for Summary Judgment, *Iver P. Cooper v. U.S. Department of Navy*, Case 1:05-cv-02252-EGS, Jul. 20, 2006.

Kang and Rokita, "Site Specific and photo-induced alkylation of DNA by a dimethylanthraquinone-oligodeoxynucleotide conjugate," Nucleic Acid Res. (Oct. 15, 1996) 24(20): 3896-902.

Supplementary European Partial Search Report for EP03788662, dated Feb. 22, 2006 (2 pages).

Landegren et al. (1988) Science 241(4869): 1077-1080.

Li et al. (2004) "DNA-templated organic synthesis: nature's strategy for controlling chemical reactivity applied to synthetic molecules," Angewandte Chemie (Intl. Ed. In English) 43(37): 4848-70.

New Engand Biolabs 1998/99 Catalog. Cover and p. 284.

Podyminogin et al., "Sequence-specific covalent modification of DNA by cross-linking oligonucleotides. Catalysis by RecA and implication for the mechanism of synaptic joint formation," Biochemistry (Oct. 10, 1995) 34(40): 13098-108.

International Search Report for Application No. PCT/US06/02420 dated Jul. 28, 2006 (3 pages).

\* cited by examiner expected mass    observed mass
13: 5705.55    5711.25 ± 9
14: 6672.18    6678.04 ± 10
15: 6363.06    6368.30 ± 9
16: 6065.81    6068.96 ± 9 expected mass    observed mass
25: 5912.61    5912.75 ± 9
26: 6718.21    6719.29 ± 10
27: 6262.54    6261.73 ± 9
28: 6486.12    6489.18 ± 9

FREE REACTANT USE IN NUCLEIC ACID-TEMPLATED SYNTHESIS

RELATED APPLICATIONS

This application claims the benefit of and priority to U.S. patent application Ser. No. 60/646,584, filed Jan. 21, 2005, the entire disclosure of which is incorporated by reference herein.

GOVERNMENT FUNDING

This invention was made with Government support under the Office of Naval Research award N00014-03-1-0749 and the National Institutes of Health award R01 GM065865. The United States Government has certain rights in the invention.

FIELD OF THE INVENTION

The invention relates generally to methods and compositions for performing nucleic acid-templated synthesis. More particularly, the invention relates to methods and compositions for performing nucleic acid-templated synthesis to produce reaction intermediates, which can then be chemically transformed into reaction products using free reactants that react with the reaction intermediates to produce the reaction products.

BACKGROUND OF THE INVENTION

Nucleic acid-templated organic synthesis enables modes of controlling reactivity that are not possible in a conventional synthesis format and allows synthetic molecules to be manipulated using translation, selection, and amplification methods previously available only to biological macromolecules (Gartner et al. (2001) J. AM. CHEM. SOC. 123: 6961-3; Gartner et al. (2002) ANGEW. CHEM., INT. ED. ENGL. 123: 61796-1800; Gartner et al. (2002) J. AM. CHEM. SOC. 124: 10304-6; Calderone et al. (2002) ANGEW. CHEM., INT. ED. ENGL. 41: 4104-8; Gartner et al. (2003) ANGEW. CHEM., INT. ED. ENGL. 42: 1370-5; Li et al. (2004) J. AM. CHEM. SOC. 124: 5090-2; Kanan et al. (2004) NATURE 431: 545-9; Gartner et al. (2004) SCIENCE 305: 1601-5; Li et al. (2004) ANGEW. CHEM. INT. ED. 43: 4848-70; Brenner et al. (1992) PROC. NATL. ACAD. SCI. USA 89: 5181; Doyon et al. (2003) J. AM. CHEM. SOC. 125: 12372-3; Halpin et al. (2004) PLoS BIOL. 2: e174). The structures that can be accessed through nucleic acid-templated synthesis, in particular, DNA-templated organic synthesis, or DTS, have been limited predominantly to products of coupling reactions between two nucleic acid-linked reactants. In some cases, however, reactants are difficult or impossible to tether to an oligonucleotide. The development of strategies that enable non-oligonucleotide linked small-molecule reagents to react in a sequence-programmed or sequence-recorded manner, therefore, would significantly expand the synthetic capabilities of nucleic acid-templated synthesis.

SUMMARY OF THE INVENTION

The present invention provides methods and compositions for expanding the scope of nucleic acid-templated organic syntheses by addressing the need for reagents to be tethered to oligonucleotides. When the linkage of reagents to a nucleic acid, for example, DNA, is not possible or convenient, these transformations allow such reagents to nevertheless contribute to small molecule syntheses while preserving the correspondence between nucleic acid sequence and the structure of the product. In addition, by decoupling the nucleic acid-templated step from the coupling reaction, this approach allows bond formation to take place under conditions that do not necessarily support nucleic acid hybridization.

In one aspect, the invention provides a method of synthesizing a reaction product. The method comprises the steps of: (a) providing a mixture comprising a first reactive unit and a second reactive unit under conditions to permit a reaction between the first and second reactive units to form a reaction intermediate; (b) providing an oligonucleotide comprising an identifying sequence attached to the reaction intermediate; and (c) combining the reaction intermediate with a free reactant selectively reactive with the reaction intermediate thereby to produce a reaction product linked to the identifying sequence. In this approach, the free reactant is more reactive with the reaction intermediate than with either of the reactive units in the starting mixture.

In another aspect, the invention provides a method of synthesizing a reaction product via nucleic acid-templated synthesis as described, for example, in U.S. patent application Ser. No. 10/643,752, which published under U.S. Patent Application Publication Number US2004/0180412. The method comprises the steps of (a) providing a mixture comprising (i) a first reactive unit attached to a first oligonucleotide comprising a codon sequence, and (ii) a second reactive unit attached to a second oligonucleotide comprising an anti-codon sequence complementary to the codon sequence; (b) annealing the codon sequence of the first oligonucleotide with the anti-codon sequence of the second oligonucleotide to induce a reaction between the first and second reactive units to form a reaction intermediate attached at least to the first oligonucleotide; and (c) combining the reaction intermediate with a free reactant selectively reactive with the reaction intermediate thereby to synthesize a reaction product still attached to the first oligonucleotide sequence. The free reactant preferably is more reactive with the reaction intermediate than with at least one of the reactive units in the starting mixture.

Similarly, to the extent that multiple different first reactive units (and optionally second reactive units) are present in the initial reaction mixture, it is possible that, under certain reaction conditions, multiple different reaction intermediates may be created. Accordingly, it may be advantageous for the free reactant to be selectively reactive with just one specific type of reaction intermediate in the mixture. Alternatively, it may be advantageous for the free reactant to be selectively reactive with a group or sub-group of reaction intermediates, where the reaction intermediates have a functional group with a particular chemical functionality. For example, the free reactant may be selectively reactive with reactive intermediates containing a free amine as compared to other reactive intermediates lacking a free amine.

Furthermore, by knowing the codon and/or anticodon sequences it is possible to determine which second reactive unit reacted with the first reactive unit to produce the reactive intermediate and/or the reaction product. Furthermore, if the first oligonucleotide provides a sequence identifier for the first reactive unit attached to the first oligonucleotide, it is possible to determine what first reaction unit reacted with the second reactive unit to produce the reaction intermediate and/or the reaction product. Based upon the reaction conditions, the reactants present in a reaction mixture containing reaction intermediates, and information concerning when certain free reactants are added to the mixture containing reaction intermediates, it can be possible to determine what free reactant reacted with a reaction intermediate to create a specific reaction product. This information can be used to identify the reaction product and the reaction pathway by which it was made.

The foregoing aspects and features of the invention may be further understood by reference to the following drawings, detailed description, examples, and claims.

DEFINITIONS

The terms, "codon" and "anti-codon" as used herein, refer to complementary oligonucleotide sequences in a template and in a transfer unit, respectively, that permit the transfer unit to anneal to the template during nucleic acid-templated synthesis.

The term, "free reactant" as used herein refers to a chemical reagent or chemical moiety that is not linked to an oligonucleotide that can participate in nucleic acid-templated synthesis. In comparison, the first and second reactive units and the transfer units are attached to oligonucleotides that can participate in nucleic acid-templated synthesis.

The terms, "oligonucleotide" or "nucleic acid" as used herein refer to a polymer of nucleotides. The polymer may include, without limitation, natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages). Nucleic acids and oligonucleotides may also include other polymers of bases having a modified backbone, such as a locked nucleic acid (LNA), a peptide nucleic acid (PNA), a threose nucleic acid (TNA) and any other polymers capable of serving as a template for an amplification reaction using an amplification technique, for example, a polymerase chain reaction, a ligase chain reaction, or non-enzymatic template-directed replication.

The term, "reactive unit" as used herein, refers to a chemical reagent or chemical moiety (including, for example, but not limited to, a building block, monomer, monomer unit, small molecule scaffold, or other reactant useful in nucleic acid-templated chemical synthesis) that can participate in a chemical reaction with another chemical reagent or chemical moiety to produce a reaction intermediate and/or a reaction product.

The term, "reaction intermediate" as used herein, refers to a chemical reagent or a chemical moiety that can be chemically transformed into a different reagent or chemical moiety with a free reactant.

The term, "small molecule" as used herein, refers to an organic compound either synthesized in the laboratory or found in nature having a molecular weight less than 10,000 grams per mole, optionally less than 5,000 grams per mole, and optionally less than 2,000 grams per mole.

The term, "small molecule scaffold" as used herein, refers to a chemical compound having at least one site or chemical moiety suitable for functionalization. The small molecule scaffold or molecular scaffold may have two, three, four, five or more sites or chemical moieties suitable for functionalization. These functionalization sites may be protected or masked as would be appreciated by one of skill in this art. The sites may also be found on an underlying ring structure or backbone. The small molecule scaffolds are not nucleic acids, nucleotides, or nucleotide analogs.

The term, "transfer unit" as used herein, refers to a molecule comprising an oligonucleotide having an anti-codon sequence attached to a reactive unit including, for example, but not limited to, a building block, monomer, monomer unit, small molecule scaffold, or other reactant useful in nucleic acid-templated chemical synthesis.

The term, "template" as used herein, refers to a molecule comprising an oligonucleotide having at least one codon sequence suitable for a nucleic acid-templated chemical synthesis. The template optionally may comprise (i) a plurality of codon sequences, (ii) an amplification means, for example, a PCR primer binding site or a sequence complementary thereto, (iii) a reactive unit associated therewith, (iv) a combination of (i) and (ii), (v) a combination of (i) and (iii), (vi) a combination of (ii) and (iii), or a combination of (i), (ii) and (iii).

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, unless specified to the contrary, two or more steps or actions may be conducted simultaneously.

DESCRIPTION OF THE DRAWINGS

FIG. 10A shows the results of the reaction of amine-linked template 13 with dansyl chloride 21 (reagents 13 and 21 are shown in FIG. 8). FIG. 10B shows the results of the reaction of amine-linked template 14 with ethyl chloroformate 22 (reagents 14 and 22 are shown in FIG. 8). FIG. 10C shows the results of the reaction of amine-linked template 15 with 4-methoxy phenyl isocyanate 23 (reagents 15 and 23 are shown in FIG. 8). FIG. 10D shows the results of the reaction of amine-linked template 16 with 6-morpholino pyridinyl 3-methoxyl phenyl isocyanate 24 (reagents 16 and 24 are shown in FIG. 8).

DETAILED DESCRIPTION

The present invention is useful in the synthesis of libraries of molecules, for example, small molecules. The functional group transformations described herein are particularly useful in expanding the scope of nucleic acid-templated organic syntheses by addressing the need for reagents to be tethered to oligonucleotides. When the linkage of reagents to an oligonucleotide is not possible or convenient, these transformations allow such reagents to nevertheless contribute to small molecule syntheses while preserving the correspondence between oligonucleotide sequence and resulting product structure.

In one aspect, the invention provides a method of synthesizing a reaction product. The method comprises the steps of: (a) providing a mixture comprising a first reactive unit and a second reactive unit under conditions to permit a reaction between the first and second reactive units to form a reaction intermediate; (b) providing an oligonucleotide comprising an identifying sequence attached to the reaction intermediate; and (c) combining the reaction intermediate with a free reactant selectively reactive with the reaction intermediate, thereby to produce a reaction product attached to the identifying sequence. In this approach, the free reactant is more reactive with the reaction intermediate than with either of the reactive units in the starting mixture.

Figure 1:
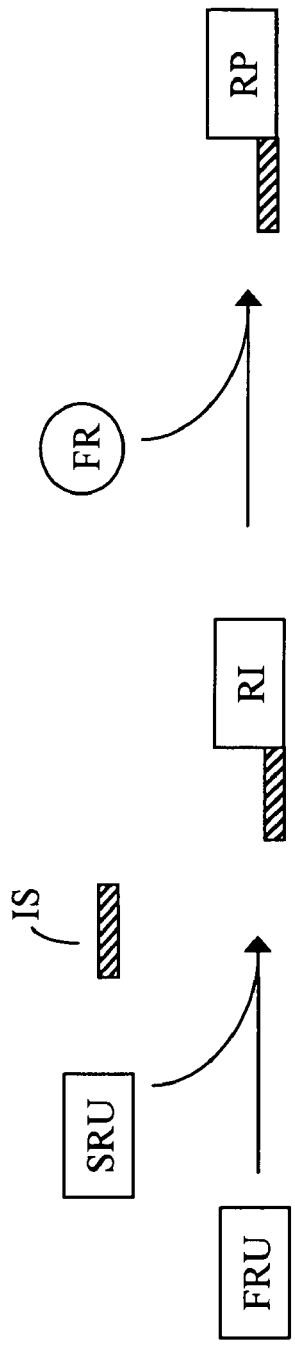
FIG. 1 is a schematic illustration of one aspect of the present invention in which a first reactive unit (FRU) and a second reactive unit (SRU) react to form a reaction intermediate (RI). The reaction intermediate (RI) is attached to an identifying sequence (IS). The RI-IS complex is combined with a free reactant (FR), which is selectively reactive with the RI to yield a reaction product (RP) linked to the IS.

This approach is shown schematically in FIG. 1. Briefly, a first reactive unit (FRU) is reacted with a second, different reactive unit (SRU) to produce a reaction intermediate (RI). The RI is attached, preferably, covalently attached, to an identifying sequence (IS). The IS can be an oligonucleotide (for example, DNA, or derivatives thereof, RNA, or derivatives thereof). Then, the RI-IS complex is combined with a free reactant (FR) under conditions to permit the FR to chemically transform the RI into a reaction product (RP). The RP is still linked to the IS, which can be used to identify RP and the synthetic history of RP.

In one approach, the IS, for example, a nucleic acid sequence defining a specific codon sequence or anti-codon sequence, is linked to the FRU prior to the reaction that produces the RI. The IS remains linked to the RI after the reaction so as to provide an IS linked to the RI. Following creation of the RP, the IS remains linked to the RP so that it is possible to identify the RP and its synthetic history. It is contemplated that the SRU may also be linked to a sequence complementary to the IS. As a result, during step (a), the IS hybridizes to the sequence complementary to the IS so as to bring the FRU and SRU into reactive proximity.

In another approach, the IS, for example, a nucleic acid sequence defining a specific codon sequence or anti-codon sequence, is linked to the RI after it has been formed by the reaction between FRU and SRU. The RI can then be chemically transformed via the FR into RP. The IS remains linked to the RP. The IS can be linked enzymatically, for example, by a polymerase or ligase, to the RI after formation of the RI.

In one embodiment, the FR is at least five times more reactive with the RI than with at least one of, and optionally all of, the reactive units or other reactive intermediates in the starting mixture. Furthermore, depending on the reactants and reaction conditions, in other embodiments the FR is at least ten times, at least fifty times, at least one hundred times, at least two hundred fifty times, at least five hundred times, or at least one thousand times more reactive with the RI than with at least one of, and optionally all of, the reactive units or other reactive intermediates in the starting mixture. In addition, depending upon the reactants and reaction conditions, the RP is synthesized with a yield greater than or equal to 50%, greater than or equal to 75%, greater than or equal to 85%, or greater than or equal to 98%.

The reactivity of the FR to the RI relative to the starting materials FRU and SRU can be determined experimentally. The amount of product produced by combining FR and RI under standard reaction conditions can be determined. The amount of product produced by combining in equimolar amounts FR with either FRU or SRU under the same reaction conditions can be determined. The yields of products can be determined by standard techniques in the chemical arts. Based on the relative amounts of product produced in each reaction it is possible to determine whether the FR is more reactive, and, if so, how much more reactive, than the FRU or the SRU. Similar approaches can be used to determine whether the free reactant is more reactive with one reaction intermediate than with other, different reactive intermediates.

In another aspect, the invention provides a method of synthesizing a reaction product via nucleic acid-templated synthesis as described, for example, in U.S. Patent Application Publication Number US2004/0180412. The method comprises the steps of (a) providing a mixture comprising (i) a first reactive unit attached to a first oligonucleotide comprising a codon sequence, and (ii) a second reactive unit attached to a second oligonucleotide comprising an anti-codon sequence complementary to the codon sequence, wherein the anti-codon sequence is indicative of the second reactive unit; (b) annealing the codon sequence of the first oligonucleotide with the anti-codon sequence of the second oligonucleotide to induce a reaction between the first and second reactive units to form a reaction intermediate attached to at least the first oligonucleotide; and (c) combining the reaction intermediate with a free reactant selectively reactive with the reaction intermediate thereby to synthesize a reaction product attached to the first oligonucleotide sequence. The free reactant preferably is more reactive with the reaction intermediate than with at least one of, and optionally all of, the reactive units or other reaction intermediates in the starting mixture.

Figure 2:
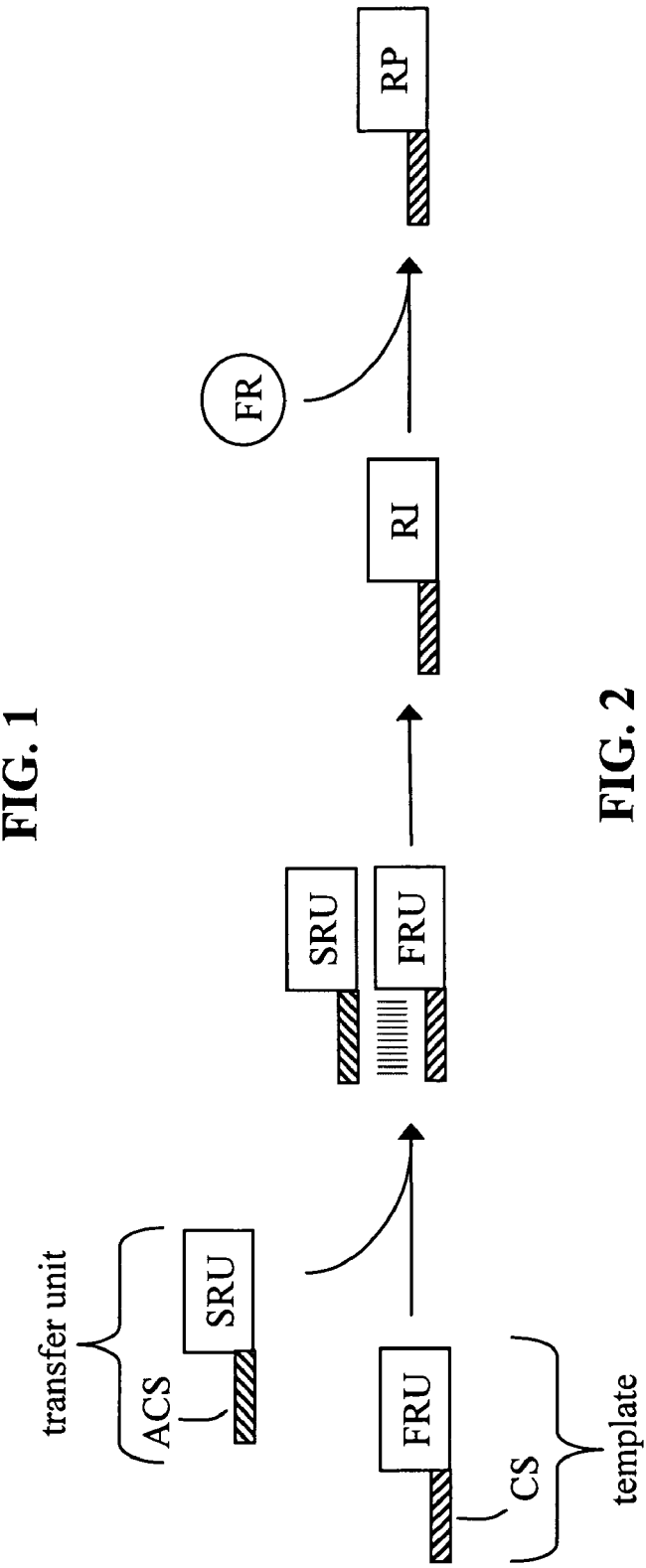
FIG. 2 is a schematic illustration of an aspect of the present invention, in which prior to the formation of the reaction intermediate (RI) the first reactive unit (FRU) and the second reactive unit (SRU) are linked to a codon sequence (CS) and a complementary anti-codon sequence (ACS), respectively. The CS and the ACS anneal to one another to permit the FRU and SRU to react with one another to produce the RI. The CS remains linked to the RI. The CS remains attached to the reaction product (RP) when the RI has been reacted with the free reactant (FR).

This approach is shown schematically in FIG. 2, where a first reactive unit (FRU) is attached, for example, covalently attached, to a first oligonucleotide comprising a codon sequence (CS). The combination of the first reactive unit and the oligonucleotide can be referred to as a template. The codon sequence may identify the FRU, for example, like an IS. Alternatively, the CS may further comprise a separate identifier sequence (IS) that identifies the FRU. In the latter scenario, the CS can identify the second reactive unit (SRU) that reacts with the FRU to create the reaction intermediate (RI) and the IS can identify the FRU.

In this approach, the SRU is attached, for example, covalently attached to a second oligonucleotide that contains an anti-codon sequence (ACS) complementary to the CS. The combination of the second reactive unit with the anti-codon sequence can be referred to as a transfer unit. When the template and the transfer unit are combined under the appropriate reaction conditions, the CS and the ACS anneal to one another to bring the FRU and SRU into reactive proximity. The FRU and SRU then react with one another, for example, by proximity catalysis, to produce RI that is still linked to CS. When combined with the free reactant (FR), the RI is chemically transformed by FR into a reaction product (RP) that is still linked to the CS. Assuming that the oligonucleotide attached to RP contains the CS, then it is possible to determine what SRU was involved in the synthesis of the RI and/or the RP. Similarly, if the oligonucleotide attached to RP contains the IS, then it is possible to determine what FRU was involved in the synthesis of the RI and/or RP. Accordingly, this information can be used to determine the identity and synthetic history of RI and/or RP.

Furthermore, it is contemplated that the FRU can be a small molecule scaffold that can be used during nucleic acid-templated synthesis to produce a small molecule. In particular, the small molecule scaffold can be used as a core on which to assemble the substituents of the small molecule.

In one embodiment, the FR is at least five times more reactive with the RI than with at least one of, and optionally all of, the reactive units or other reactive intermediates in the starting mixture. Furthermore, depending on the reactants and reaction conditions, in other embodiments the FR is at least ten times, at least fifty times, at least one hundred times, at least two hundred fifty times, at least five hundred times, or at least one thousand times more reactive with the RI than with at least one of, and optionally all of, the reactive units or other reactive intermediates in the starting mixture. In addition, depending upon the reactants and reaction conditions, the RP is synthesized with a yield greater than or equal to 50%, greater than or equal to 75%, greater than or equal to 85%, or greater than or equal to 98%.

In another aspect, the invention provides a method of synthesizing a reaction product. The method comprises the steps of: (a) providing a mixture of a population of different first reactive units and a second reactive unit under conditions that induce a reaction between at least one of the first reactive units and the second reactive unit, thereby to form a reaction intermediate co-existing with the population of first reactive units; (b) providing an identifying sequence attached to the reaction intermediate, wherein the sequence distinguishes the reaction intermediate from the first reactive units; and combining the reaction intermediate co-existing with the first reactive units with a free reactant capable of selectively reacting with the reaction intermediate, thereby synthesizing a reaction product linked to an identifying sequence, the reaction product co-existing with the population of first reactive units. The free reactant is more reactive with the reaction intermediate than with at least one of the reactive units or other reactive intermediates in the starting mixture.

Figure 3:
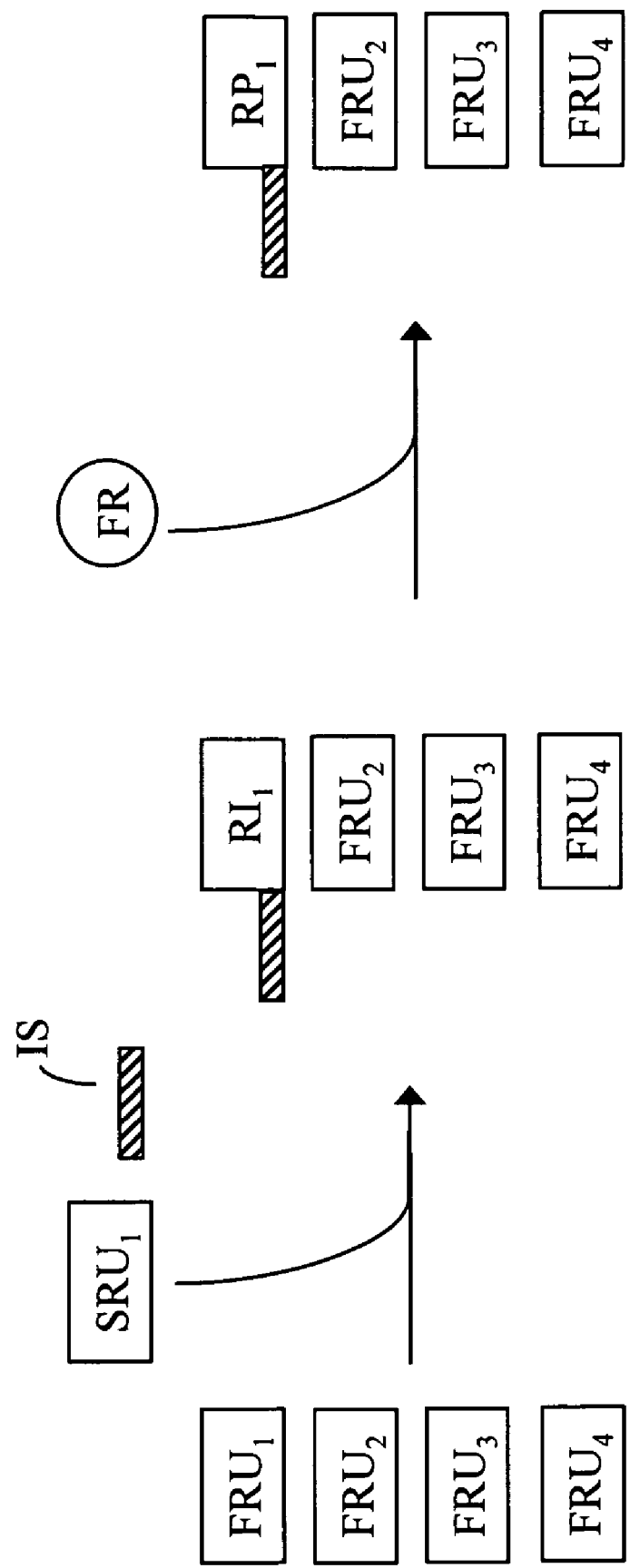
FIG. 3 is a schematic illustration of an embodiment of the scheme shown in FIG. 1, in which, in a mixture of a population of first reactive units ($FRU_1$-$FRU_4$), at least one of the first reactive units ($FRU_1$) reacts with a second reactive unit ($SRU_1$) to form a reaction intermediate ($RI_1$) which coexists with the population of first reactive units ($FRU_2$-$FRU_4$). The reaction intermediate ($R_1$) is linked to an identifying sequence (IS). The reaction intermediate ($RI_1$) linked to the IS and coexisting with the population of first reactive units ($FRU_2$-$FRU_4$) then is permitted to react with a free reactant (FR), which is selectively reactive with $RI_1$ to yield a reaction product ($RP_1$) linked to the IS.

This approach is shown schematically in FIG. 3 and is similar to the approach shown schematically in FIG. 1 except that the first reaction unit is present as a mixture of first reactive units. Briefly, a starting mixture containing four first reactive units denoted $FRU_1$, $FRU_2$, $FRU_3$, and $FRU_4$ are combined with a second reactive unit denoted as $SRU_1$. Under the appropriate conditions, $FRU_1$ and $SRU_1$ react with one another to produce a reaction intermediate denoted as $RI_1$. An identifier sequence (IS) can be attached to the $RI_1$ which identifies $RI_1$. Thereafter, a free reactant (FR) is combined to the mixture under conditions for the RI to be chemically transformed into a reaction product denoted $RP_1$. The $RP_1$ is still linked to the IS which can be used to identify RP and the synthetic history of RP. In addition, it is contemplated that $RP_1$ can be exposed to other rounds of functional group transformations, especially where the FRU is a small molecule scaffold, to produce further modified products.

In another aspect, the invention provides a method of synthesizing a reaction product via nucleic acid-templated synthesis. The method comprises the steps of: (a) providing a mixture comprising (i) a plurality of different first reactive units each linked to first oligonucleotides comprising a codon sequence, wherein each oligonucleotide sequence is also indicative of the first reactive unit attached thereto; (b) providing a second reactive unit attached to a second oligonucleotide comprising an anti-codon sequence complementary to the codon sequence of at least one first reactive unit, wherein the anti-codon sequence is indicative of the second reactive unit; (c) annealing the codon sequence of at least one of the first oligonucleotides with the anti-codon sequence of the second oligonucleotide to induce a reaction between the first and second reactive units to form a first reaction intermediate linked at least to a first oligonucleotide; and (d) combining the first reaction intermediate with a free reactant selectively reactive with the first reaction intermediate, thereby synthesizing a first reaction product linked to the identifying sequence, wherein the free reactant is more reactive with the first reaction intermediate than with at least one of, and optionally all of, the reactive units or other reactive intermediates in the mixture.

Figure 4:
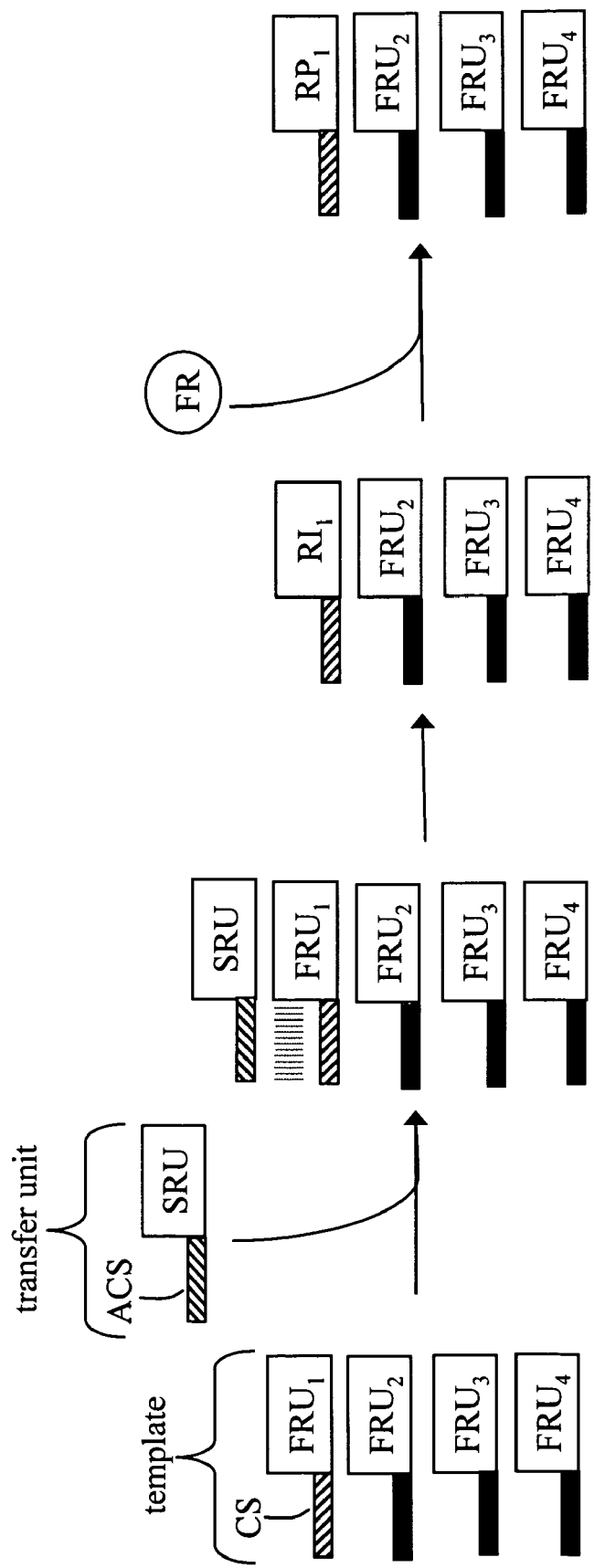
FIG. 4 is a schematic illustration of an embodiment of the scheme shown in FIG. 2, in which prior to the formation of the reaction intermediate ($R_1$) the first reactive units ($FRU_1$-$FRU_4$) and the second reactive unit (SRU) are linked to codon sequences (CS) and a complementary anti-codon sequence (ACS), respectively. The CS remains linked to $RI_1$. The CS remains attached to the reaction product ($RP_1$) when $RI_1$ has been reacted with the free reactant (FR) to produce $RP_1$.

This approach is shown schematically in FIG. 4 and is similar to the approach shown schematically in FIG. 2 except the first reactive unit is present as a mixture of first reactive units. Briefly, the initial reaction contains a plurality of templates, where each template contains a first reactive unit (denoted as $FRU_1$, $FRU_2$, $FRU_3$ and $FRU_4$) attached, preferably, covalently attached, to its own respective oligonucleotide containing its own codon unique sequence (CS). The oligonucleotide preferably also contains an identifier sequence (IS) that identifies what first reactive unit is attached to what codon sequence of the template. A transfer unit containing a second reactive unit (SRU) attached, preferably, covalently attached, to an oligonucleotide containing an anti-codon sequence complementary to the codon sequence is combined with the templates. The ACS of the transfer unit anneals to the CS of the template to bring the $FRU_1$ and SRU into reactive proximity, whereupon the $FRU_1$ and SRU react with one another to produce reaction intermediate ($RI_1$) that still remains attached to the oligonucleotide containing the CS. When combined with the free reactant (FR), the RI is chemically transferred by the FR to produce the reaction product (RP) that is still linked to the CS. Assuming that the oligonucleotide attached to the RP contains a CS, then it is possible to determine what SRU was involved in the synthesis of RI and/or the RP. Similarly, if the oligonucleotide attached to RP contains the IS, then it is possible to determine what FRU was involved in the synthesis of the RI and/or the RP. Accordingly, this information can be used to determine the identity and synthetic history of RI and/or RP. As discussed, it is contemplated that the first reactive units can be small molecule scaffolds useful in the design and synthesis of a small molecule library.

In addition, it is possible that multiple different functional group transformations can occur simultaneously in the same reaction vessel. Accordingly, the method can also include the additional steps of: providing a third different reactive unit linked to a third oligonucleotide comprising an anti-codon sequence complementary to the codon sequence of at least one different first reactive unit, wherein the anti-codon sequence is indicative of the third reactive unit; annealing the codon sequence of a different one of the first oligonucleotides with the anti-codon sequence of the third oligonucleotide to induce a reaction between the first and third reactive units to form a second reaction intermediate attached at least to a first, different oligonucleotide; and combining the second reaction intermediate with a free reactant selectively reactive with the second reaction intermediate, thereby synthesizing a second reaction product attached to the identifying sequence, wherein the free reactant is more reactive with the second reaction intermediate than with at least one of, and optionally all of, the reactive units or other reactive intermediates in the mixture.

In addition, it is contemplated that the reaction products can be exposed to other rounds of functional group transformations, for example, where $FRU_1$ is a small molecule scaffold, to produce further modified products.

As will be appreciated by those skilled in the art, the method of the invention can be used to expand the range of chemistries that can be used during nucleic acid-templated chemical syntheses. General considerations concerning the selection and use of templates, transfer units, reaction conditions, reaction chemistries, selection procedures are know in the art. A general discussion of these considerations follows.

I. Template Considerations

The nucleic acid template can direct a wide variety of chemical reactions without obvious structural requirements by sequence-specifically recruiting reactants linked to complementary oligonucleotides. During synthesis, the template hybridizes or anneals to one or more transfer units to direct the synthesis of a reaction intermediate that can subsequently be converted by a free reactant into a reaction product. The reaction product then is selected or screened based on certain criteria, such as the ability to bind to a preselected target molecule. Once the reaction product has been identified, the associated template can then be sequenced to decode the synthetic history of the reaction intermediate and/or the reaction product.

(i) Template Format

The length of the template may vary greatly depending upon the type of the nucleic acid-templated synthesis contemplated. For example, in certain embodiments, the template may be from 10 to 10,000 nucleotides in length, from 20 to 1,000 nucleotides in length, from 20 to 400 nucleotides in length, from 40 to 1,000 nucleotides in length, or from 40 to 400 nucleotides in length. The length of the template will of course depend on, for example, the length of the codons, the complexity of the library, the complexity and/or size of a reaction product, the use of spacer sequences, etc.

The template may incorporate a hairpin loop on one end terminating in a reactive unit that can interact with one or more reactive units associated with transfer units. For example, a DNA template can comprise a hairpin loop terminating in a 5'-amino group, which may or may not be protected. The amino group may act as an initiation point for formation of an unnatural polymer or small molecule.

(ii) Codon Usage

It is contemplated that the sequence of the template may be designed in a number of ways. For example, the length of the codon must be determined and the codon sequences must be set. If a codon length of two is used, then using the four naturally occurring bases only 16 possible combinations are available to be used in encoding the library. If the length of the codon is increased to three (the number Nature uses in encoding proteins), the number of possible combinations increases to 64. If the length of the codon is increased to four, the number of possible combinations increases to 256. Other factors to be considered in determining the length of the codon are mismatching, frame-shifting, complexity of library, etc. As the length of the codon is increased up to a certain point the number of mismatches is decreased; however, excessively long codons likely will hybridize despite mismatched base pairs.

Although the length of the codons may vary, the codons may range from 2 to 50 nucleotides, from 2 to 40 nucleotides, from 2 to 30 nucleotides, from 2 to 20 nucleotides, from 2 to 15 nucleotides, from 2 to 10 nucleotides, from 3 to 50 nucleotides, from 3 to 40 nucleotides, from 3 to 30 nucleotides, from 3 to 20 nucleotides, from 3 to 15 nucleotides, from 3 to 10 nucleotides, from 4 to 50 nucleotides, from 4 to 40 nucleotides, from 4 to 30 nucleotides, from 4 to 20 nucleotides, from 4 to 15 nucleotides, from 4 to 10 nucleotides, from 5 to 50 nucleotides, from 5 to 40 nucleotides, from 5 to 30 nucleotides, from 5 to 20 nucleotides, from 5 to 15 nucleotides, from 5 to 10 nucleotides, from 6 to 50 nucleotides, from 6 to 40 nucleotides, from 6 to 30 nucleotides, from 6 to 20 nucleotides, from 6 to 15 nucleotides, from 6 to 10 nucleotides, from 7 to 50 nucleotides, from 7 to 40 nucleotides, from 7 to 30 nucleotides, from 7 to 20 nucleotides, from 7 to 15 nucleotides, from 7 to 10 nucleotides, from 8 to 50 nucleotides, from 8 to 40 nucleotides, from 8 to 30 nucleotides, from 8 to 20 nucleotides, from 8 to 15 nucleotides, from 8 to 10 nucleotides, from 9 to 50 nucleotides, from 9 to 40 nucleotides, from 9 to 30 nucleotides, from 9 to 20 nucleotides, from 9 to 15 nucleotides, from 9 to 10 nucleotides. Codons, however, preferably are 3, 4, 5, 6, 7, 8, 9 or 10 nucleotides in length.

A set of codons used in the template preferably maximizes the number of mismatches between any two codons within a codon set to ensure that only the proper anti-codons of the transfer units anneal to the codon sites of the template. Furthermore, it is important that the template has mismatches between all the members of one codon set and all the codons of a different codon set to ensure that the anti-codons do not inadvertently bind to the wrong codon set. The choice of exemplary codon sets and methods of creating functional codon sets are described, for example, in U.S. Patent Publication No. US 2004/0180412. Using this and other approaches, different sets of codons can be generated so that no codons are repeated.

When the nucleic acid-templated synthesis is used to produce a polymer or a small molecule, spacer sequences may also be placed between the codons to prevent frame shifting. For example, the bases of the template that encode a polymer subunit (the "genetic code" for the polymer) may be chosen so as to minimize the possibility of out-of-frame annealing. These genetic codes reduce undesired frameshifted nucleic acid-templated polymer translation and differ in the range of expected melting temperatures and in the minimum number of mismatches that result during out-of-frame annealing.

(iii) Template Synthesis

The templates may be synthesized using methodologies well known in the art. These methods include both in vivo and in vitro methods including PCR, plasmid preparation, endonuclease digestion, solid phase synthesis (for example, using an automated synthesizer), in vitro transcription, strand separation, etc. Following synthesis, the template, when desired may be attached (for example, covalently or non covalently attached) with a reactive unit of interest using standard coupling chemistries known in the art.

An efficient method to synthesize a large variety of templates is to use a "split-pool" technique. The oligonucleotides are synthesized using standard 3' to 5' chemistries. First, the constant 3' end is synthesized. This is then split into n different vessels, where n is the number of different codons to appear at that position in the template. For each vessel, one of the n different codons is synthesized on the (growing) 5' end of the constant 3' end. Thus, each vessel contains, from 5' to 3', a different codon attached to a constant 3' end. The n vessels then are pooled, so that a single vessel contains n different codons attached to the constant 3' end. Any constant bases adjacent the 5' end of the codon are now synthesized. The pool then is split into m different vessels, where m is the number of different codons to appear at the next (more 5') position of the template. A different codon is synthesized (at the 5' end of the growing oligonucleotide) in each of the m vessels. The resulting oligonucleotides are pooled in a single vessel. Splitting, synthesizing, and pooling are repeated as required to synthesize all codons and constant regions in the oligonucleotides.

II. Transfer Units

A transfer unit comprises an oligonucleotide containing an anti-codon sequence and a reactive unit. The anti-codons are designed to be complementary to the codons present in the template. Accordingly, the sequences used in the template and the codon lengths should be considered when designing the anti-codons. Any molecule complementary to a codon used in the template may be used, including natural or non-natural nucleotides. In certain embodiments, the codons include one or more bases found in nature (i.e., thymidine, uracil, guanidine, cytosine, and adenine). Thus, the anti-codon can include one or more nucleotides normally found in Nature with a base, a sugar, and an optional phosphate group.

As discussed above, the anti-codon is associated with a particular type of reactive unit to form a transfer unit. The reactive unit may represent a distinct entity or may be part of the functionality of the anti-codon unit. In certain other embodiments, where a small molecule library is to be created rather than a polymer library, the anti-codon generally is associated with a reactive unit or reactant used to modify a small molecule scaffold. In certain embodiments, the reactant is linked to the anti-codon via a linker long enough to allow the reactant to come into reactive proximity with the small molecule scaffold. The linker preferably has a length and composition to permit intramolecular reactions but yet minimize intermolecular reactions. The reactants include a variety of reagents as demonstrated by the wide range of reactions that can be utilized in nucleic acid-templated synthesis and can be any chemical group, catalyst (e.g., organometallic compounds), or reactive moiety (e.g., electrophiles, nucleophiles) known in the chemical arts.

In certain embodiments, each anti-codon sequence is associated with one monomer type. For example, the anti-codon sequence ATTAG may be associated with a carbamate residue with an isobutyl side chain, and the anti-codon sequence CATAG may be associated with a carbamate residue with a phenyl side chain. This one-for-one mapping of anti-codon to monomer units allows the decoding of any polymer of the library by sequencing the nucleic acid template used in the synthesis and allows synthesis of the same polymer or a related polymer by knowing the sequence of the original polymer. By changing (e.g., mutating) the sequence of the template, different monomer units may be introduced, thereby allowing the synthesis of related polymers, which can subsequently be selected and evolved. In certain preferred embodiments, several anti-codons may code for one monomer unit as is the case in Nature.

The anti-codon can be associated with the reactant through a linker moiety. The linkage can be cleavable by light, oxidation, hydrolysis, exposure to acid, exposure to base, reduction, etc. Fruchtel et al. (1996) ANGEW. CHEM. INT. ED. ENGL. 35: 17 describes a variety of linkages useful in the practice of the invention. The linker facilitates contact of the reactant with the small molecule scaffold and in certain embodiments, depending on the desired reaction, positions DNA as a leaving group ("autocleavable" strategy), or may link reactive groups to the template via the "scarless" linker strategy (which yields product without leaving behind an additional atom or atoms having chemical functionality), or a "useful scar" strategy (in which a portion of the linker is left behind to be functionalized in subsequent steps following linker cleavage). Useful linkers, their design and use are described in U.S. Patent Application Publication No. US 2004/0180412.

The specific annealing of transfer units to templates permits the use of transfer units at concentrations lower than concentrations used in many traditional organic syntheses. Thus, transfer units can be used at submillimolar concentrations (e.g. less than 100 µM, less than 10 µM, less than 1 µM, less than 100 nM, or less than 10 nM).

III. Chemical Reactions

A variety of compounds and/or libraries can be prepared using the methods described herein. In certain embodiments, compounds that are not, or do not resemble, nucleic acids or analogs thereof, are synthesized according to the method of the invention. In certain other embodiments, compounds that are not, or do not resemble, proteins, peptides, or analogs thereof, are synthesized according to the method of the invention.

(i) Coupling Reactions for Small Molecule Synthesis

In some embodiments, it is possible to create compounds such as small molecules using the methods described herein. These small molecules may be like natural products, non-polymeric, and/or non-oligomeric. The substantial interest in small molecules is due in part to their use as the active ingredient in many pharmaceutical preparations although they may also be used, for example, as catalysts, materials, or additives.

In synthesizing small molecules using the method of the present invention, an evolvable template can be used. The template can include a small molecule scaffold upon which the small molecule is to be built, or a small molecule scaffold may be added to the template. The small molecule scaffold can be any chemical compound with two or more sites for functionalization. For example, the small molecule scaffold can include a ring system (e.g., the ABCD steroid ring system found in cholesterol) with functionalizable groups coupled to the atoms making up the rings. In another example, the small molecule may be the underlying structure of a pharmaceutical agent such as morphine, epothilone or a cephalosporin antibiotic. The sites or groups to be functionalized on the small molecule scaffold may be protected using methods and protecting groups known in the art. The protecting groups used in a small molecule scaffold may be orthogonal to one another so that protecting groups can be removed one at a time.

In this approach, the transfer units comprise an anti-codon associated with a reactant or a building block for use in modifying, adding to, or taking away from the small molecule scaffold. The reactants or building blocks may be, for example, electrophiles (e.g., acetyl, amides, acid chlorides, esters, nitriles, imines), nucleophiles (e.g., amines, hydroxyl groups, thiols), catalysts (e.g., organometallic catalysts), or side chains. The transfer units are allowed to contact the template under hydridizing conditions. As a result of oligonucleotide annealing, the attached reactant or building block is allowed to react with a site on the small molecule scaffold to produce one or more reaction intermediates. The reaction intermediates can then be reacted with a free reactant to produce a reaction product.

The reaction conditions, linker, reactant, and site to be functionalized are chosen to avoid intermolecular reactions and accelerate intramolecular reactions. Sequential or simultaneous contacting of the template with transfer units can be employed depending on the particular compound to be synthesized.

After the sites on the scaffold have been modified, the newly synthesized small molecule remains associated with the template that encoded its synthesis. Decoding the sequence of the template permits the deconvolution of the synthetic history and thereby the structure of the small molecule. The template can also be amplified in order to create more of the desired small molecule and/or the template can be evolved (mutagenized) to create related small molecules. The small molecule can also be cleaved from the template for purification or screening.

(ii) Coupling Reactions for Polymer Synthesis

In certain embodiments, polymers, specifically unnatural polymers, can be prepared using the techniques described herein. Exemplary unnatural polymers include, but are not limited to, peptide nucleic acid (PNA) polymers, polycarbamates, polyureas, polyesters, polyacrylate, polyalkylene (e.g., polyethylene, polypropylene), polycarbonates, polypeptides with unnatural stereochemistry, polypeptides with unnatural amino acids, and combination thereof. In certain embodiments, the polymers comprise at least 10, 25, 75, 100, 125, 150 monomer units or more. The polymers synthesized using the methodologies described herein may be used, for example, as catalysts, pharmaceuticals, metal chelators, or catalysts.

In preparing certain unnatural polymers, the monomer units attached to the anti-codons may be any monomers or oligomers capable of being joined together to form a polymer. The monomer units may be, for example, carbamates, D-amino acids, unnatural amino acids, PNAs, ureas, hydroxy acids, esters, carbonates, acrylates, or ethers.

(iii) Reaction Conditions

It is understood that nucleic acid-templated reactions, for example, nucleic acid-templated reactions to produce reaction intermediates, can occur in aqueous or non-aqueous (i.e., organic) solutions, or a mixture of one or more aqueous and non-aqueous solutions. In aqueous solutions, reactions can be performed at pH ranges from about 2 to about 12, or preferably from about 2 to about 10, or more preferably from about 4 to about 10. The reactions used in DNA-templated chemistry preferably should not require very basic conditions (e.g., pH>12, pH>10) or very acidic conditions (e.g., pH<1, pH<2, pH<4), because extreme conditions may lead to degradation or modification of the nucleic acid template and/or molecule (for example, the polymer, or small molecule) being synthesized. The aqueous solution can contain one or more inorganic salts, including, but not limited to, NaCl, $Na_2SO_4$, KCl, $Mg^{+2}$, $Mn^{+2}$, etc., at various concentrations.

Organic solvents suitable for nucleic acid-templated reactions include, but are not limited to, methylene chloride, chloroform, dimethylformamide, and organic alcohols, including methanol and ethanol. To permit quantitative dissolution of reaction components in organic solvents, quaternized ammonium salts, such as, for example, long chain tetraalkylammonium salts, can be added (Jost et al. (1989) NUCLEIC ACIDS RES. 17: 2143; Mel'nikov et al. (1999) LANGMUIR 15: 1923-1928).

Nucleic acid-templated reactions may require a catalyst, such as, for example, homogeneous, heterogeneous, phase transfer, and asymmetric catalysis. In other embodiments, a catalyst is not required. The presence of additional, accessory reagents not linked to a nucleic acid are preferred in some embodiments. Useful accessory reagents can include, for example, oxidizing agents (e.g., $NaIO_4$); reducing agents (e.g., $NaCNBH_3$); activating reagents (e.g., EDC, NHS, and sulfo-NHS); transition metals such as nickel (e.g., $Ni(NO_3)_2$), rhodium (e.g. $RhCl_3$), ruthenium (e.g. $RuCl_3$), copper (e.g. $Cu(NO_3)_2$), cobalt (e.g. $CoCl_2$), iron (e.g. $Fe(NO_3)_3$), osmium (e.g. $OsO_4$), titanium (e.g. $TiCl_4$ or titanium tetraisopropoxide), palladium (e.g. $NaPdCl_4$), or Ln; transition metal ligands (e.g., phosphines, amines, and halides); Lewis acids; and Lewis bases.

Reaction conditions preferably are optimized to suit the nature of the reactive units and oligonucleotides used. It is understood that the choice of reagents, for example, free reactants, and the reaction conditions used to create the reaction intermediates and to convert the reaction intermediates into final products will depend upon the particular compounds and libraries to be produced. It is contemplated, however, that the choice of reagents and reaction conditions is within the level of skill in the art.

(iv) Classes of Chemical Reactions

It is understood that a large variety of chemical reactions can be used to create the reaction intermediates and/or to create the reaction products from the reaction intermediates. Known chemical reactions for synthesizing polymers, small molecules, or other molecules can be used in nucleic acid-templated reactions. Thus, reactions such as those listed in *March's Advanced Organic Chemistry, Organic Reactions, Organic Syntheses*, organic text books, journals such as *Journal of the American Chemical Society, Journal of Organic Chemistry, Tetrahedron, etc.*, and Carruther's *Some Modern Methods of Organic Chemistry* can be used. The chosen reactions preferably are compatible with nucleic acids such as DNA or RNA or are compatible with the modified nucleic acids used as the template.

Notwithstanding the foregoing, it is contemplated that the invention is particularly useful in performing certain functional group transformations, which include, without limitation, azide-to-amine transformations, azide-to-thiol transformations, azide-to-carboxylic acid transformations, hydroxyl-to-amine transformations, hydroxyl-to-thiol transformations, acetal-to-aldehyde transformations, ketal-to-ketone transformations, carbonate-to-hydroxyl group transformations, carbamate-to-amine transformations, thiocarbonate-to-thiol transformations, nitro group-to-amine transformations, sulfonamide-to-amine transformations, alkene-to-epoxide transformations, $\alpha,\beta$-unsaturated ketone-to-epoxide transformations, epoxide-to-1,2-diol transformations, epoxide-to-1,2-hydroxy amine transformations, epoxide-to-1,2-hydroxy sulfide transformations, alkene-to-aziridine transformations, aziridine-to-1,2-diamine transformations, aziridine-to-1,2-amino sulfide transformations, phosphonate ester-to-phosphonic acid transformations, imide-to-amine transformations, and nitrile-to-carboxylic acid transformations. Other exemplary transformations may be found, for example, in Greene et al. (ed.) (1999) PROTECTIVE GROUPS IN ORGANIC SYNTHESIS 3RD ED., Wiley-Interscience, and in Kocienski (1994) PROTECTING GROUPS, Thieme.

IV. Selection, Screening and Identification of Products (i) Selection and Screening Approaches Selection and/or screening for reaction products with desired activities (such as catalytic activity, binding affinity, or a particular effect in an activity assay) may be performed using methodologies known and used in the art. For example, affinity selections may be performed according to the principles used in library-based selection methods such as phage display, polysome display, and mRNA-fusion protein displayed peptides. Selection for catalytic activity may be performed by affinity selections on transition-state analog affinity columns (Baca et al. (1997) PROC. NATL. ACAD. SCI. USA 94(19): 10063-8) or by function-based selection schemes (Pedersen et al. (1998) PROC. NATL. ACAD. SCI. USA 95(18): 10523-8). Since minute quantities of DNA (~$10^{-20}$ mol) can be amplified by PCR (Kramer et al. (1999) CURRENT PROTOCOLS IN MOLECULAR BIOLOGY (ed. Ausubel, F. M.) 15.1-15.3, Wiley), these selections can be conducted on a scale ten or more orders of magnitude less than that required for reaction analysis by current methods, making a truly broad search both economical and efficient.

The templates and reaction products can be selected (or screened) for binding to a target molecule. In this context, selection or partitioning means any process whereby a library member bound to a target molecule is separated from library members not bound to target molecules. Selection can be accomplished by various methods known in the art.

The templates of the present invention contain a built-in function for direct selection and amplification. In most applications, binding to a target molecule preferably is selective, such that the template and the resulting reaction product bind preferentially with a specific target molecule, perhaps preventing or inducing a specific biological effect. Ultimately, a binding molecule identified using the present invention may be useful as a therapeutic and/or diagnostic agent. Once the selection is complete, the selected templates optionally can be amplified and sequenced. The selected reaction products, if present in sufficient quantity, can be separated from the templates, purified (e.g., by HPLC, column chromatography, or other chromatographic method), and further characterized.

The selection strategy can be carried out to allow selection against almost any target. Importantly, the selection strategy does not require any detailed structural information about the target molecule or about the molecules in the libraries. The entire process is driven by the binding affinity involved in the specific recognition and binding of the molecules in the library to a given target.

The linkage between the template molecule and reaction product allows rapid identification of binding molecules using various selection strategies. Nucleic acid-templated syntheses broadly permit identifying binding molecules for any known target molecule. In addition, novel unknown targets can be discovered by isolating binding molecules against unknown antigens (epitopes) and using these binding molecules for identification and validation.

Selection of binding molecules from a library can be performed in any format to identify optimal binding molecules. Binding selections typically involve immobilizing the desired target molecule, adding a library of potential binders, and removing non-binders by washing. When the molecules showing low affinity for an immobilized target are washed away, the molecules with a stronger affinity generally remain attached to the target. The enriched population remaining bound to the target after stringent washing is preferably eluted with, for example, acid, chaotropic salts, heat, competitive elution with a known ligand or by proteolytic release of the target and/or of template molecules. The eluted templates are suitable for PCR, leading to many orders of amplification, whereby essentially each selected template becomes available at a greatly increased copy number for cloning, sequencing, and/or further enrichment or diversification.

The target molecule (peptide, protein, DNA or other antigen) can be immobilized on a solid support, for example, a container wall, a wall of a microtiter plate well. The library preferably is dissolved in aqueous binding buffer in one pot and equilibrated in the presence of immobilized target molecule. Non-binders are washed away with buffer. Those molecules that may be binding to the target molecule through their attached DNA templates rather than through their synthetic moieties can be eliminated by washing the bound library with unfunctionalized templates lacking PCR primer binding sites. Remaining bound library members then can be eluted, for example, by denaturation.

Alternatively, the target molecule can be immobilized on beads, particularly if there is doubt that the target molecule will adsorb sufficiently to a container wall, as may be the case for an unfolded target eluted from an SDS-PAGE gel. The derivatized beads can then be used to separate high-affinity library members from nonbinders by simply sedimenting the beads in a benchtop centrifuge. Alternatively, the beads can be used to make an affinity column. In such cases, the library is passed through the column one or more times to permit binding. The column then is washed to remove nonbinding library members. Magnetic beads are essentially a variant on the above; the target is attached to magnetic beads which are then used in the selection.

Library members that bind a target molecule can be released by denaturation, acid, or chaotropic salts. Alternatively, elution conditions can be more specific to reduce background or to select for a desired specificity. Elution can be accomplished using proteolysis to cleave a linker between the target molecule and the immobilizing surface or between the reaction product and the template. Also, elution can be accomplished by competition with a known competitive ligand for the target molecule. Alternatively, a PCR reaction can be performed directly in the presence of the washed target molecules at the end of the selection procedure. Thus, the binding molecules need not be elutable from the target to be selectable since only the template is needed for further amplification or cloning, not the reaction product itself. Indeed, some target molecules bind the most avid ligands so tightly that elution would be difficult.

(ii) Identification of Products

Once all rounds of selection are complete, the templates which are, or formerly were, attached to the selected reaction product preferably are amplified using any suitable technique to facilitate sequencing or other subsequent manipulation of the templates. Natural oligonucleotides can be amplified by any state of the art method. These methods include, for example, polymerase chain reaction (PCR); nucleic acid sequence-based amplification (see, for example, Compton (1991) NATURE 350: 91-92), amplified anti-sense RNA (see, for example, van Gelder et al. (1988) PROC. NATL. ACAD. SCI. USA 85: 77652-77656); self-sustained sequence replication systems (Gnatelli et al. (1990) PROC. NATL. ACAD. SCI. USA 87: 1874-1878); polymerase-independent amplification (see, for example, Schmidt et al. (1997) NUCLEIC ACIDS RES. 25: 4797-4802, and in vivo amplification of plasmids carrying cloned DNA fragments. Descriptions of PCR methods are found, for example, in Saiki et al. (1985) SCIENCE 230: 1350-1354; Scharf et al. (1986) SCIENCE 233: 1076-1078; and in U.S. Pat. No. 4,683,202. Ligase-mediated amplification methods such as Ligase Chain Reaction (LCR) may also be used. In general, any means allowing faithful, efficient amplification of selected nucleic acid sequences can be employed in the method of the present invention. It is preferable, although not necessary, that the proportionate representations of the sequences after amplification reflect the relative proportions of sequences in the mixture before amplification.

For non-natural nucleotides the choices of efficient amplification procedures are fewer. As non-natural nucleotides can be incorporated by certain enzymes including polymerases it will be possible to perform manual polymerase chain reaction by adding the polymerase during each extension cycle.

Once amplified, the sequences of the template that encoded a product of interest can be determined. Sequencing, for example, can be performed by a standard dideoxy chain termination method, or by chemical sequencing, for example, using the Maxam-Gilbert sequencing procedure. Alternatively, the sequence of the template (or, if a long template is used, the variable portion(s) thereof) can be determined by hybridization experiments. For example, a single-stranded template molecule associated with a detectable moiety such as a fluorescent moiety is exposed to a chip bearing a large number of clonal populations of single-stranded nucleic acids or nucleic acid analogs of known sequence, each clonal population being present at a particular addressable location on the chip. The template sequences are permitted to anneal to the chip sequences. The position of the detectable moieties on the chip then is determined. Based upon the location of the detectable moiety and the immobilized sequence at that location, the sequence of the template can be determined. It is contemplated that large numbers of such oligonucleotides can be immobilized in an array on a chip or other solid support.

Libraries can be evolved by introducing mutations at the DNA level, for example, using error-prone PCR (Cadwell et al. (1992) PCR METHODS APPL. 2: 28) or by subjecting the DNA to in vitro homologous recombination (Stemmer (1994) PROC. NATL. ACAD. SCI. USA 91: 10747; Stemmer (1994) NATURE 370: 389) or by cassette mutagenesis. Template evolution and evolutionary synthesis are described, for example, in U.S. patent application, Publication No. US 2004/0180412.

The following examples contain important additional information, exemplification and guidance that can be adapted to the practice of this invention in its various embodiments and equivalents thereof. Practice of the invention will be more fully understood from these following examples, which are presented herein for illustrative purpose only, and should not be construed as limiting in anyway.

EXAMPLES

The following examples demonstrate the feasibility of sequence programmed functional group transformations. Examples 1 and 2 describe three sequence-programmed functional group transformations, namely-azide to-amine, azide-to-thiol, and azide-to-carboxylic acid transformations where the end products of the transformations have been characterized by gel electrophoresis (Example 1) or by mass spectrometry (Example 2). Example 3 shows that it is possible to transform amine-linked templates into a sulfonamide, a carbamate, a urea or a thiourea using small molecule reagents, for example, sulfonyl chloride, chloroformate, isocyanate, and isothiocyanate reactants not linked to DNA. Example 4 shows that it is possible to sequence-specifically transform, in a single-solution, a mixture of organic azides into amine intermediates and then sequence-specifically transform the amine intermediates into sulfonamide, carbamate, urea, and thiourea products using free reactants (e.g., sulfonyl chloride, chloroformate, isocyanate, and isothiocyanate) not linked to DNA.

Example 1

DNA-Templated Transformation of Azides into Primary Amines, Carboxylic Acids, and Thiols (Characterization by PAGE)

Figure 5A:
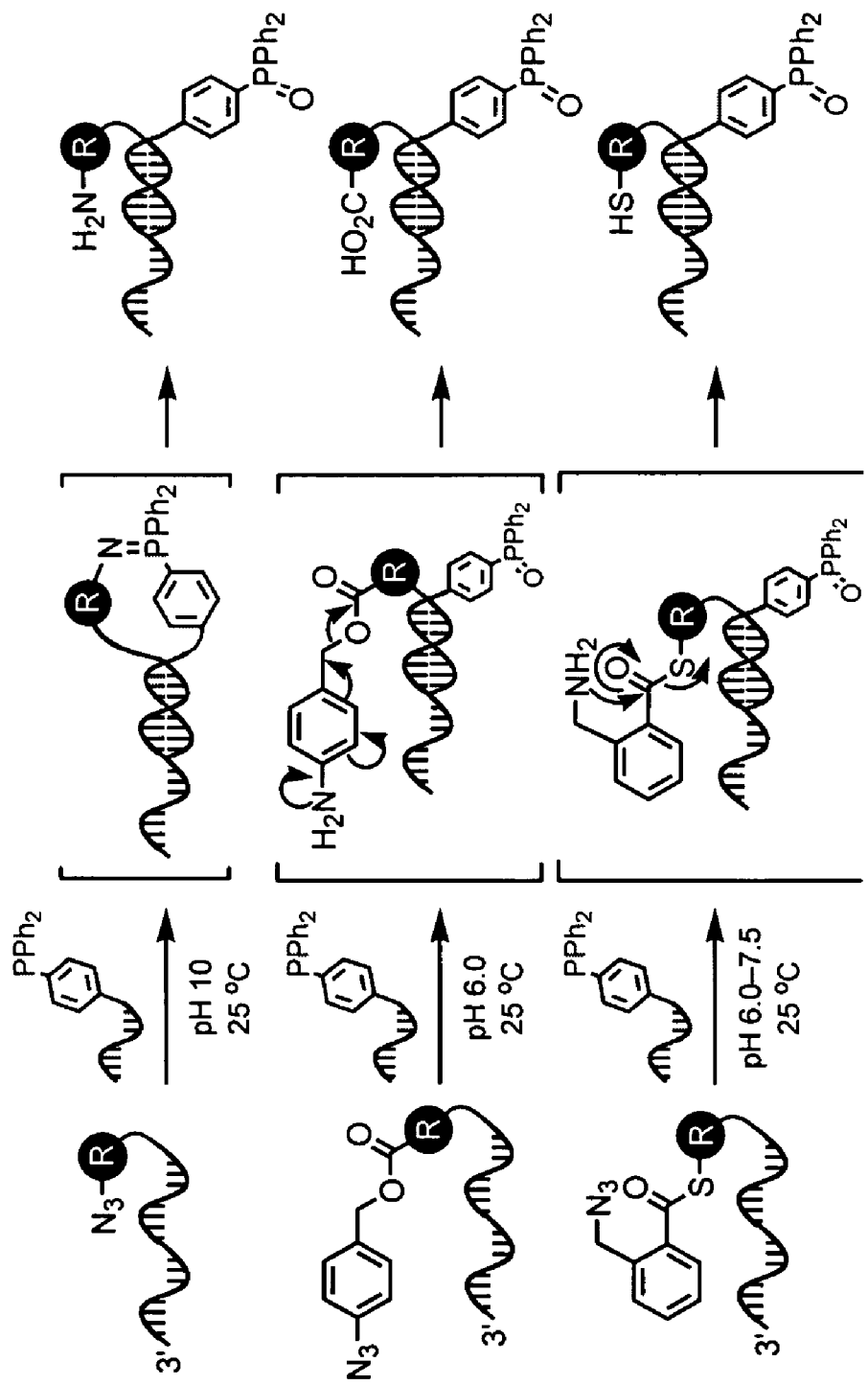
FIG. 5A depicts DNA-templated transformation of azides into primary amines (top scheme), carboxylic acids (middle scheme), and thiols (bottom scheme).

This example describes sequence-programmed functional group transformations where an azide can be specifically converted into an amine, a thiol, or a carboxylic acid. The individual reaction schemes and the resulting reaction yields are shown in FIGS. 5A and 5B.

I. Materials and Methods (i) Synthesis of Azido Acids

Figure 5B:
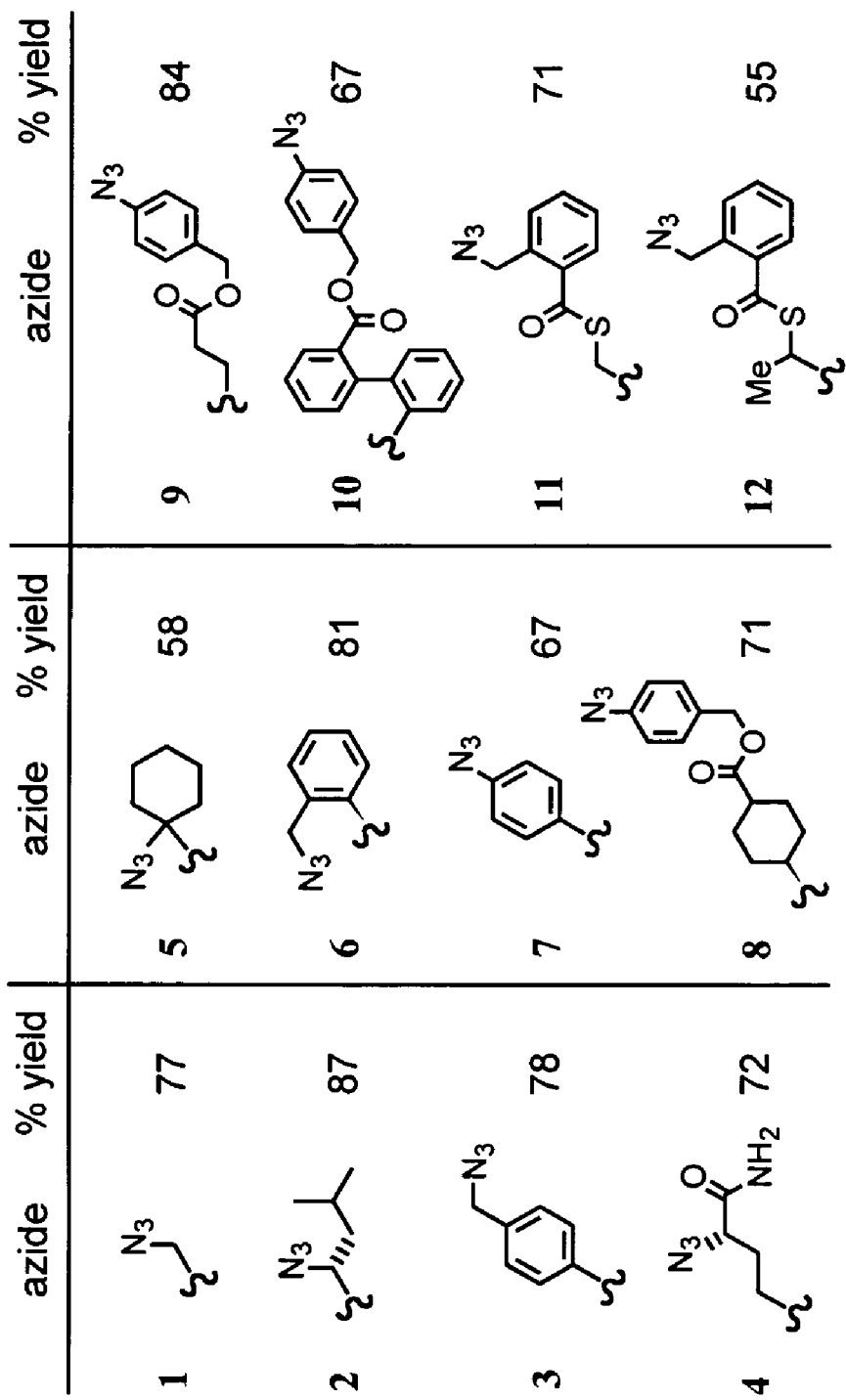
FIG. 5B depicts exemplary DNA-templated reactions using substrate azides 1-12, in which the listed yields represent lower limits.

Azido substrates for the synthesis of compounds 1-12 shown in FIG. 5B were prepared from the corresponding carboxylic acid precursors as follows:

Azido Acetic Acid (Used to produce template 1 in FIG. 5B). This reagent was produced as described in Lundquist et al. (2001) ORG LETT. 3: 781. The product was found to have the following characteristics: $^1$H NMR (300 MHz, CDCl$_3$) δ 3.96 (2H, s).

Azido-3-Methyl Pentanoic Acid (Used to produce template 2 in FIG. 5B). This reagent was produced as described in Lundquist et al. (2001) supra. The product was found to have the following characteristics: $^1$H NMR (300 MHz, CDCl$_3$) δ 3.92 (1H, br), 3.88 (2H, dd, J=5.7 Hz, J=9 Hz), 1.77 (2H, m), 0.99 (6H, t, J=6.6 Hz).

4-Azidomethylbenzoic Acid (Used to prepare template 3 in FIG. 5B). Sodium azide (1.3 g, 20 mmol) and 18-crown-6 ether (0.2 mL, 1 mmol) were dissolved in DMSO (4 mL). To the resulting solution was added 4-chloromethyl benzoic acid (1.71 g, 10 mmol) and the reaction mixture was stirred 12 h at 25° C. The reaction was diluted in EtOAc, washed with 0.1 N HCl (2×), then washed with brine. The organic layer was dried with Na$_2$SO$_4$ and concentrated to provide a white solid (1.75 g, quant.). The resulting product was found to have the following characteristics: $^1$H NMR (300 MHz, CDCl$_3$) δ 8.15 (2H, d, J=8.4 Hz) 7.45 (2H, d, J=8.4 Hz) (1H, s); ESMS calculated for C$_8$H$_6$N$_3$O$_2$: 176.0460. observed: 176.0461.

1-Azidocyclohexyl Carboxylic Acid (Used to prepare template 5 in FIG. 5B) and Azidoisoglutamic Acid (Used to prepare template 4 in FIG. 5B) were synthesized according to the method described for the synthesis of azido acids by diazo transfer in Lundquist et al. (2001) supra. 1-azidocyclohexyl carboxylic acid was found to have the following characteristics: $^1$H NMR (300 MHz, CDCl$_3$) δ 1.86 (4H, m) 1.63 (4H, m) 1.36 (2H, m); CIMS calculated for C$_7$H$_7$N$_3$O$_2$ (M+NH$_4$$^+$): 1187.1195. observed: 1187.1188. Azidoisoglutamic acid was found to have the following characteristics: $^1$H NMR (300 MHz, CDCl$_3$) δ 6.43 (2H, d, J=17.4 Hz) 3.14 (1H, dd, J=14.1 Hz, J=6.9 Hz) 2.54 (2H, tJ=7.5 Hz) 2.23 (2H, dd, J=13.6 Hz J=6.6 Hz); CIMS calculated for C$_7$H$_7$N$_3$O$_2$ (M+NH$_4$$^+$): 190.0931. observed: 190.040.

1-Azido Methyl Benzoic Acid (Used to produce template 6 in FIG. 5B). This reagent was produced as described in Wada et al. (2001) TETRAHEDRON LETT. 42: 1069-72, and also in Love et al. (2001). J. ORG CHEM. 66: 68165-76. The product was found to have the following characteristics: $^1$H NMR (300 MHz, CDCl$_3$) δ 8.18 (1H, dd, J=7.6 Hz, J=1.2 Hz), 7.63 (1H td, J=7.5 Hz, J=1.2 Hz), 7.55 (1H, d, J=6.6 Hz), 7.46 (1H, td, J=7.5 Hz, J=1.5 Hz), 4.894 (2H, s).

4-Azidobenzoic Acid (Used to produce template 7 in FIG. 5B). This reagent was purchased from Sigma-Aldrich (St. Louis, Mo.).

4-Azidobenzyl-Cyclohexyl Dicarboxylic Acid Monoester (Used to prepare template 8 in FIG. 5B). Trans-cyclohexyl dicarboxylic acid (200 mg, 1.16 mmol), EDC (223 mg, 2.32 mmol), and N,N-diisopropylethylamine (0.4 mL, 2.32 mmol) were dissolved in CH$_2$Cl$_2$ (4 mL) and stirred for 30 min at 25° C. To this mixture was added 4-azido benzyl alcohol (86.6 mg, 0.58 mmol). The reaction was stirred 12 h at 25° C. The reaction mixture was concentrated and purified by flash chromatography (30% EtOAc/hexanes). The desired ester was obtained as a yellow solid (18.2 mg, 5%). The resulting product was found to have the following characteristics: $^1$H NMR (300 MHz, CDCl$_3$) δ 7.34 (2H, d, J=8.4 Hz) 7.03 (2H, d, J=8.4 Hz) 5.08 (1H, s) 2.33 (2H, m) 2.09 (4H, d, J=9.3 Hz) 1.47 (4H, t, J=9.9 Hz); ESM calculated for C$_{15}$H$_{17}$N$_3$O$_4$ (M+HCO$_2$$^-$): 348.1196. observed: 348.1195.

4-Azidobenzyl-Succinic Acid Monoester (Used to prepare template 9 in FIG. 5B). 4-Azidobenzyl alcohol (100 mg, 0.67 mmol), succinic anhydride (134 mg, 1.37 mmol), and N,N-dimethylaminopyridine (3.7 mg, 30 μmol) were dissolved in DMF (1 mL) and stirred 12 h at 25° C. The reaction mixture was concentrated and purified by flash chromatography (30% EtOAc/hexanes). The desired ester was obtained as yellow solid (75.9 mg, 45%). The resulting product was found to have the following characteristics: $^1$H NMR (300 MHz, CDCl$_3$) δ 7.28 (2H, d, J=7.8 Hz) 6.96 (2H, d, J=7.8 Hz), 5.05 (2H, s), 2.63 (4H, m); ESMS calculated for C$_7$H$_6$N$_3$O$_2$. 248.0672. observed: 248.0660.

4-Azidobenzyl-Diphenicacid Monoester (Used to prepare template 10 in FIG. 5B). 4-Azidobenzyl alcohol (112 mg, 0.5 mmol) and diphenic acid anhydride (74.5 mg, 0.5 mmol) were dissolved in pyridine (1 mL) and stirred 12 h at 25° C. The reaction mixture was diluted in EtOAc, washed with phosphate buffer (pH 6.0, 2×), then washed with brine. The organic layer was dried over Na$_2$SO$_4$ and concentrated in vacuo. The crude product was purified by flash chromatography (25% EtOAc/hexanes). The desired ester was obtained as yellow solid (193 mg, 99%). The resulting product was found to have the following characteristics: $^1$H NMR (300 MHz, CDCl$_3$) δ 9.87 (1H, s) 7.92 (1H, dd, J=7.2Hz, J=1.2 Hz) 7.86 (1H, dd, J=7.8 Hz, J=1.2 Hz) 7.43 (2H, dd, J=5.7 Hz, J=1.5 Hz) 7.38 (2H, dd, J=5.7 Hz, J=1.2 Hz) 7.32 (2H, dd, J=7.5 Hz, J=1.2 Hz) 7.28 (2H, dd, J=7.3 Hz, J=1.2 Hz) 6.98 (2H, J=8.4

Hz) 6.85 (2H, J=8.4 Hz) 4.91 (2H, J=2.7 Hz); ESMS calculated for $C_{21}H_{16}N_3O_4$ (M+H$^+$): 374.1141. observed: 374.1149.

1-Azidomethylbenzoyl Thio Acetic Acid Thioester (Used to prepare template 11 in FIG. 5B). 2-Azidomethylbenzoyl acid (40 mg, 0.23 mmol) was mixed with EDC (64.9 mg, 0.34 mmol) and N-hydroxysuccinimide (NHS) (39.1 mg, 0.34 mmol) in $CH_2Cl_2$ at 25° C. for 2 h. The reaction mixture was washed with $NaHCO_3$ (2×), then washed with brine. The organic layer was concentrated and the crude product was directly used in the next step without further purification. N-hydroxylsuccinimidyl 2-azidomethyl benzoate ester (16.4 mg, 47 μmol) and thioacetic acid (3.2 μL) in DMF (250 μL) were allowed to react at 25° C. for 24 h. The reaction mixture was diluted in EtOAc and washed with $NaHCO_3$ (2×), then washed with brine. The organic layer was dried with $Na_2SO_4$ and concentrated in vacuo. The crude mixture was purified by flash chromatography (30% EtOAc/hexanes) to provide the thioester (9.8 mg, 83%). The resulting product was found to have the following characteristics: $^1H$ NMR (300 MHz, $CDCl_3$) δ 7.95 (d, 1H, J=7.8 Hz) 7.56 (t, 1H, J=7.8 Hz) 7.50 (d, 1H, J=6.6 Hz) 7.41 (t, 1H, J=7.8 Hz) 4.64 (s, 2H) 3.88 (s, 2H); ESMS calculated for $C_7H_6N_3O_2$: 250.0287. observed: 250.084.

2-Azidomethylbenzoyl Thio Propionic Acid Thioester (Used to prepare template 12 in FIG. 5B). 2-azidomethylbenzoyl N-hydroxy succinimidyl (NHS) ester was prepared by mixing equal volumes of 1-azido methyl benzoic acid (used to produce template 6 in FIG. 5B) (900 mM in DMF), EDC (900 mM in DMF) and NHS (900 mM in DMF) at 25° C. for 1 h. The thiol group was attached to the DNA oligonucleotide in a parallel preparation, and was incorporated into the template upon template formation (see below, preparation for 5' 2-azidomethylbenzoyl thio propionic acid thioester-linked DNA).

(ii) Preparation of Functionalized Oligonucleotides

Throughout this Example and the following Examples, oligonucleotides were synthesized on a Perseptive Biosystems Expedite 8090 DNA synthesizer using standard phosphoramidite protocols and purified using preparative scale reverse-phase HPLC. Reagents for automated solid-phase oligonucleotide synthesis were purchased from Glen Research. For amine-terminated and biotinylated DNA oligonucleotides described below, 5' amino-modifier 5 (Glen Research) was used to prepare 5' amino-modified oligonucleotides; 3' amino-modifier C7 CPG (Glen Research) was used to prepare 3' amino-modified oligonucleotides; and biotin TEG CPG (Glen Research) was used to prepare 3' biotin-labeled oligonucleotides. Functionalized DNA oligonucleotides were purified by analytical scale reverse-phase HPLC.

Concentrations of purified oligonucleotides in solution were determined based on their absorbance at 260 nm measured on a Hewlett-Packard 8453 UV-visible spectrophotometer (Agilent Technologies). Oligonucleotides stained with ethidium bromide were visualized and quantitated by UV transillumination and densitometry using an Eagle Eye II densitometer (Stratagene).

(a) Template Oligonucleotides

5' Azide-Linked DNA Oligonucleotide Templates (Used to produce templates 1-11 in FIG. 5B). The N-hydroxy succinimidyl (NHS) ester of the desired azido acid was prepared by mixing equal volumes of the respective azido acid (900 mM in DMF), EDC (900 mM in DMF) and NHS (900 mM in DMF) at 25° C. for 1 h. The crude NHS ester was added in two portions (50 μL each) to a solution containing 5' amino-modified DNA oligonucleotide (50 μL, typically 300 μM) in 100 mM sodium phosphate buffer (pH 7.2, 350 μL). The 30-mer template used in these preparations was 5'NH$_2$ ($C_2H_4O)_2$—$PO_3H$-GGT ACG AAT TGC ACT CGG GAA ATC CAC CTT (SEQ ID NO: 1). The coupling reaction was performed at 25° C. for 1 h. The resulting reaction mixture was directly loaded onto a NAP-5 size exclusion column (Amersham Biosciences) to remove organic solvent, salts, and excess small molecules, and the azide-linked DNA oligonucleotides were further purified by analytical scale reverse-phase HPLC (8-30% MeCN/0.1 M TEAA gradient). The desired oligonucleotide products were characterized by MALDI-TOF mass spectrometry.

5' 2-Azidomethylbenzoyl Thio Propionic Acid Thioester-Linked DNA (Used to produce template 12 in FIG. 5B). A solution of 2,2'-dithiodipropionic acid in DMF (900 mM) was mixed with equal volumes of EDC (900 mM in DMF) and NHS (900 mM in DMF) at 25° C. for 1 h. The crude NHS ester (50 μL) was added to a solution containing 5' amino-modified DNA oligonucleotide (50 μL, typically 300 μM) in 100 mM sodium phosphate buffer (pH 7.2, 350 μL). The coupling reaction was performed at 25° C. for 1 h. The reaction mixture was directly loaded onto a NAP-5 size exclusion column (Amersham Biosciences) and purified by analytical scale reverse-phase HPLC (8-30% MeCN/0.1 M TEAA gradient). The disulfide-linked oligonucleotide product was characterized by MALDI-TOF mass spectrometry. The 2-thiopropionic acid-linked oligonucleotide was prepared by treating the disulfide-linked oligonucleotide above (typically 10 μM) in 100 mM CAPS buffer (pH 8) with 20 mM DTT at 25° C. for 0.5 h. Excess DTT was removed by passing the reaction mixture through a gel filtration column. In parallel, 2-azidomethylbenzoyl N-hydroxy succinimidyl (NHS) ester was prepared as described (see above, preparation for 2-Azidomethylbenzoyl Thio Propionic Acid Thioester). The crude NHS ester (100 μL) was added to a solution of 5' thiol-linked oligonucleotide (100 μL) in 100 mM sodium phosphate buffer (pH 7.2, 300 μL). The coupling reaction was performed at 25° C. for 1 h. The reaction mixture was directly loaded onto a NAP-5 size exclusion column and purified by analytical scale reverse-phase HPLC (8-30% MeCN/0.1 M TEAA gradient). The desired oligonucleotide product was characterized by MALDI-TOF mass spectrometry.

(b) Transfer Units

3' Triphenylphosphine-Linked DNA. Attachment of the triphenylphosphine group was performed on 3' amino-modified oligonucleotides linked to CPG resin. A 10-mer reagent fully complementary to the template had the structure 5' AAT TCG TAC C-OPO$_3$H—$CH_2CH(CH_2OH)(CH_2)_4$NHCOC$_6H_4$PPh$_2$ (SEQ ID NO: 2). A 10-mer reagent containing a three-base mismatch relative to the template had the following structure—5' AAT ACA TCC C-OPO$_3$H—$CH_2CH(CH_2OH)(CH_2)_4$NHCOC$_6H_4$PPh$_2$ (SEQ ID NO: 3). The latter was used as a control in these experiments.

The Fmoc group on 3' FMOC-NH-oligonucleotides was removed by three cycles of: (i) treatment with 20% piperidine in DMF for 10 min; (ii) washing with DMF; and (iii) washing with MeCN. The resin was dried under a stream of nitrogen gas. A solution of 4-diphenylphosphino benzoic acid (30.6 mg, 100 μmol), EDC (19.1 mg, 100 μmol), N,N-diisopropylethylamine (36.8 μL, 211 μmol) in DMF (0.6 mL) was added to the resin and the mixture was incubated at 37° C. for 2 h. The resin was washed with DMF (2×) and with MeCN (2×), then dried under nitrogen. The derivatized oligonucleotide was cleaved from the CPG resin by incubation in 1:1 ammonium hydroxide:methyl amine (AMA) with tris(2-carboxyethyl)phosphine hydrochloride (TCEP-HCl, 1 mg) at 55° C. for 45 min. The cleavage solution was filtered and purified by analytical scale reverse-phase HPLC (8-30% MeCN/0.1 M TEAA gradient). The desired oligonucleotide products were characterized by MALDI-TOF mass spectrometry.

(c) Capture Reagents

In order to perform polyacrylamide gel electrophoresis, the reaction products were captured using 20-mer secondary reagents (capture reagents) that annealed to the template.

Amino-modified DNA (This reagent was used to capture the products of the templates 8-10). The 20-mer secondary reagent contained the sequence 5' TCC CGA GTG CAA TTC GTA CC-OPO$_3$H—CH$_2$CH(CH$_2$OH)(CH$_2$)$_4$NH$_2$ (SEQ ID NO: 4). This oligonucleotide was used as a starting material for the following capture reagents.

3' Bromoacetate-Linked DNA (This reagent was used to capture the products of the templates 11 and 12). The NHS ester of bromoacetic acid was prepared by mixing equal volumes of 900 mM bromoacetic acid in DMF, 900 mM EDC in DMF, and 900 mM NHS in DMF at 25° C. for 1 h. The crude NHS ester (100 μL) was added to a solution of 5' amino-modified DNA oligonucleotide (50 μL, typically 300 μM) in 100 mM sodium phosphate buffer (pH 7.2, 350 μL). The coupling reaction was allowed to proceed at 25 C for 1 h. The reaction mixture was directly loaded onto a NAP-5 size exclusion column to remove organic solvent, salts, and excess small molecules and was further purified by analytical scale reverse-phase HPLC (8-30% MeCN/0.1 M TEAA gradient). The desired oligonucleotide products were characterized by MALDI-TOF mass spectrometry.

3' 4-Formylbenzoate-Linked DNA (This reagent was used to capture the products of the template 7). The 4-formylbenzoate linked 20-mer DNA was prepared following the protocol for bromoacetate-linked DNA using 4-formyl benzoic acid instead of bromoacetic acid.

3' Succinic Acid Monoester-Linked DNA (This reagent was used to capture the products of the templates 1-6). Succinic anhydride (22 mg, 0.1 mmol) was activated with NHS (10 mg, 0.1 mmol) in DMF (200 μL) at 25° C. for 15 min. 100 μL of the mixture was added to the 3' amino modified template (50 μL, typically 300 μM) in 100 mM HEPES buffer (pH 8.5; 850 μL) and was incubated at 37° C. for 16 h. The reaction mixture was desalted by NAP-5 size exclusion column and further purified by analytical scale HPLC (8-30% MeCN/0.1 M TEAA gradient). The desired oligonucleotide products were characterized by MALDI-TOF mass spectrometry.

II. Results and Conclusions (i) DNA-Templated Transformation from an Azide to an Amine A variety of organic azides linked to the 5' termini of 30-mer DNA oligonucleotide templates were reacted with a triphenylphosphine conjugated to the 3' terminus of a complementary DNA 10-mer (see, FIG. 5A). DNA-templated azide-to-amine functional group transformations were performed by mixing a 30-mer 5' azide-linked template (12 pmol) and 10-mer 3' triphenylphosphine-linked reagent (24 pmol) in a total volume of 200 μL of 100 mM CAPS buffer (pH 10) containing 500 mM NaCl at 25° C. for 16 h. For substrates 4 and 5, 1 M NaCl and the addition of 0.5 mM DTT to inhibit phosphine oxidation was found to increase yields. Representative reaction conditions included for 1-7, 60 nM azide, 120 nM phosphine, 0.1 M CAPS pH 10, 0.5 M NaCl; for 8-11, as above, except 0.1 M MES pH 6.0, 1 M NaCl; and for 12, as above, except 0.1 M MOPS pH 7.5, 1 M NaCl.

Unlike DNA-templated coupling reactions, the azide-to-amine transformations could not be monitored directly by denaturing polyacrylamide gel electrophoresis (PAGE) because the starting materials and products had similar molecular weights. To assay the progress of these reactions, the putative amine products were captured with 20-mer-linked carboxylic acids in the presence of a carbodiimide, or with 20-mer-linked aldehydes in the presence of NaBH$_3$CN. These secondary reagents or capture reagents displaced the 10-mer linked phosphine oxide and efficiently coupled with primary amines, but not with azides. The resulting amide or secondary amine products gained the molecular weight of the 20-mer and could easily be distinguished from starting azides by PAGE.

In order to capture amine products derived from substrates 1-6 a 20-mer 3' carboxylic acid-linked reagent (24 pmol) was added to the reaction mixture with EDC (30 mM) and sulfo-NHS (15 mM) in MES buffer (pH 6.5). In order to capture amine products derived from substrate 7, the product was captured with a 20-mer 3' aldehyde-linked reagent in the presence of NaBH$_3$CN (3 mM) in MES buffer (pH 6.5). Following product capture, the DNA-linked species were precipitated with NaOAc (pH 5), ethanol, and glycogen.

The resulting pellets were dissolved in denaturing gel-loading buffer and were subjected to denaturing PAGE analysis. Unless specified, denaturing PAGE analysis was performed using 15% polyacrylamide gel (TBE-urea).

Reaction yields were quantitated by ethidium bromide staining of the gels, UV visualization and CCD-based densitometry of product and template bands. Yield calculations assumed that templates and products in denaturing gels stained with equal intensity per base. In cases where products were partially double-stranded during quantitation, changes in staining intensity may result in higher apparent yields.

Typical results obtained by denaturing PAGE analysis are shown in FIG. 6. FIG. 6A shows denaturing PAGE analysis of a DNA-templated azide-to-amine transformation for azide 3 in FIG. 5B. FIG. 6B shows denaturing PAGE analysis of a DNA-templated azide-to-amine transformation for azide 7 in FIG. 5B.

For the seven azides tested (substrates 1-7 in FIG. 5B), DNA-templated azide reduction proceeded efficiently at pH 10. The actual yields of the reaction products are summarized in FIG. 5B. In each case, control reactions in which the phosphine was linked to a non-complementary, mismatched oligonucleotide did not generate significant amide or secondary amine products, indicating that these DNA-templated azide-to-amine transformations proceed sequence-specifically.

(ii) DNA-Templated Transformation from an Azide to Carboxylic Acid or Thiol

The scope of the reactions was further extended to effect azide-to carboxylic acid and azide-to-thiol functional group transformations (see, FIG. 5A). In both cases, azide reduction induced spontaneous fragmentation to unmask carboxylic acid or thiol groups. To assess the efficiency of these reactions, DNA-linked amines were used to capture carboxylic acids (products resulting from substrates 8-10) in the presence of a carbodiimide, while DNA-linked alkyl bromides were used to capture thiol products (products resulting from substrates 11 and 12).

Figure 6A:
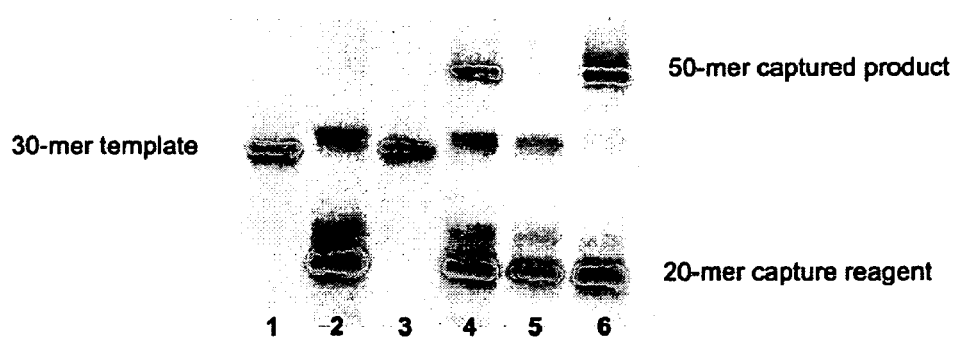
FIG. 6A is a representation of a denaturing polyacrylamide gel electrophoresis (PAGE) gel following DNA-templated azide-to-amine transformation of azide 3 from FIG. 5B. Lane 1 contains azide-linked 30-mer template. Lane 2 contains azide-linked 30-mer template+carboxylic acid-linked 20-mer capture reagent+30 mM EDC+15 mM sulfo-NHS (showing no product formation). Lane 3 contains azide-linked 30-mer template+phosphine-linked 10-mer reagent (10-mer not visible). Lane 4 contains azide-linked 30-mer template+phosphine-linked 10-mer reagent+carboxylic acid-linked 20-mer capture reagent+30 mM EDC+15 mM sulfo-NHS, the 50-mer secondary product arising from azide-to-amine transformation following by DNA-templated amine acylation is visible. Lane 5 contains azide-linked 30-mer template+phosphine-linked 10-mer reagent containing a mismatched sequence+carboxylic acid-linked 20-mer capture reagent+30 mM EDC+15 mM sulfo-NHS. Lane 6 contains azide-linked 30-mer template+5 mM TCEP-HCl+carboxylic acid-linked 20-mer capture reagent+30 mM EDC+15 mM sulfo-NHS (positive control in which the azide is reduced in situ by TCEP). It appears that incomplete denaturing of the duplex between the 30-mer template and 20-mer capture reagent at the onset of electrophoresis results in band blurring (lanes 2 and 4-6).
Figure 6B:
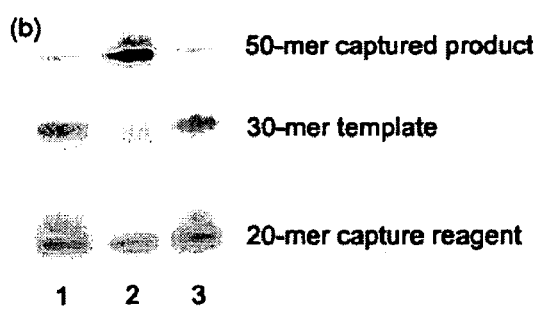
FIG. 6B is a representation of a denaturing PAGE gel following DNA-templated azide-to-amine transformation of azide 7 from FIG. 5B. Lane 1 contains azide-linked 30-mer template+aldehyde-linked 20-mer capture reagent+3 mM $NaBH_3CN$. Lane 2 contains azide-linked 30-mer template+ phosphine-linked 10-mer reagent+aldehyde-linked 20-mer capture reagent+3 mM $NaBH_3CN$. Lane 3 contains azide-linked 30-mer template+phosphine-linked 10-mer reagent containing a mismatched sequence+aldehyde-linked 20-mer capture reagent+3 mM $NaBH_3CN$. Slight 50-mer captured product formation is observed in lanes 1 and 3, which arises from slow spontaneous reduction of the phenyl azide during the preparation of a substrate-linked template and during the DNA-templated reactions. The background reactivity observed in lanes 1 and 3 (<13%) was subtracted to determine the reported yield for lane 2.
Figure 6C:
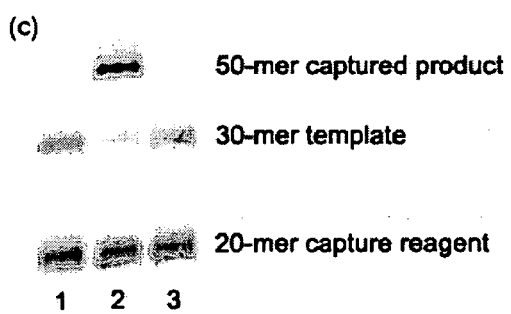
FIG. 6C is a representation of a denaturing PAGE gel following DNA-templated azide-to-carboxylic acid transformation of azide 8 from FIG. 5B. Lane 1 contains azide-linked 30-mer template+amine-linked 20-mer capture reagent+30 mM EDC+15 mM sulfo-NHS. Lane 2 contains azide-linked 30-mer template+phosphine-linked 10-mer reagent+amine-linked 20-mer capture reagent+30 mM EDC+15 mM sulfo-NHS. Lane 3 contains azide-linked 30-mer template+phosphine-linked 10-mer reagent containing a mismatched sequence+amine-linked 20-mer capture reagent+30 mM EDC+15 mM sulfo-NHS.

DNA-templated azide-to-carboxylic acid transformations were performed like the azide-to-amine transformations, except that the buffer contained 0.1 M MES pH 6.0 and 1 M NaCl. To capture carboxylic acid products, 20-mer 3' amine-linked reagent was added to the reaction mixture with EDC (30 mM) and sulfo-NHS (15 mM) in MES buffer (pH 6.5). Typical results from denaturing PAGE are shown in FIG. 6C (represented is the case using reagent 8 from FIG. 5B).

Figure 6D:
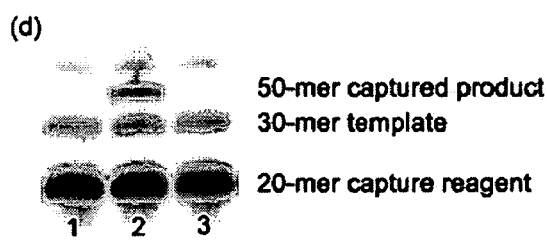
FIG. 6D is a representation of a denaturing PAGE gel following DNA-templated azide-to-thiol transformation of azide 11 from FIG. 5B using a 10% polyacrylamide gel. Lane 1 contains azide-linked 30-mer template+alkyl bromide-linked 20-mer capture reagent. Lane 2 contains azide-linked 30-mer template+phosphine-linked 10-mer reagent+alkyl bromide-linked 20-mer capture reagent. Lane 3 contains azide-linked 30-mer template+phosphine-linked 10-mer reagent containing a mismatched sequence+alkyl bromide-linked 20-mer capture reagent.

DNA-templated azide-to-thiol transformations were performed as above, except that the buffer contained either 0.1 M MES pH 6.0 (for substrate 11) or MOPS pH 7.5 (for substrate 12) and 1 M NaCl. To capture thiol products, 20-mer 3' alkyl bromide-linked reagent was added to the reaction mixture and incubated at 37° C. for 6 h. Typical results from denaturing PAGE are shown in FIG. 6D (represented is the case using reagent 11 from FIG. 5B).

For the carboxylic acid-to-amine and thiol-to-amine transformations, denaturing PAGE analysis indicated that DNA-templated functional group transformations to unmask carboxylic acid and thiol groups (substrates 8-12 in FIG. 5B) also proceeded efficiently and sequence-specifically.

Example 2

DNA-Templated Transformation of Azides into Primary Amines, Carboxylic Acids, and Thiols (Characterization by Mass Spectrometry)

This Example is similar to Example 1 except the reaction products were characterized by mass spectrometry rather than PAGE. To facilitate this a smaller template and different capture system were used under the same or similar conditions.

I. Materials and Methods
(i) Synthesis of Azido Acids
The azido substrates for the synthesis of compounds 1-12 shown in FIG. 5B were prepared as described in Example 1.
(ii) Preparation of Functionalized Oligonucleotides
The oligonucleotides used in this Example were prepared in a manner similar to Example 1 with the following changes.
(a) Template Oligonucleotides
The template oligonucleotides were prepared as described in Example 1 except that rather than using a 30-mer template, the following 10-mer template was used: 5'-NH$_2$(C$_2$H$_4$O)$_2$—PO$_3$H-GGT ACG AAT T-OPO$_3$H—CH(CH$_2$OH)CH$_2$(OC$_2$H$_4$)$_4$CH$_2$NHCO-biotin (SEQ ID NO: 5).
(b) Transfer Units
The triphenylphosphine-linked reagent was prepared as described in Example 1.
(iii) Mass Spectroscopic Analysis
MALDI-TOF mass spectrometry was performed on an Applied Biosystems Voyager-DE Pro Biospectrometry Workstation and processed with Voyager Data Explorer software. A mixture of nine parts hydroxypicolinic acid (HPA, 50 mg/mL in 50% MeCN/H$_2$O) and one part ammonium citrate (50 mg/mL in H$_2$O) was used as the matrix in all experiments.

II. Results and Conclusions
Complementary DNA-linked phosphine reagent (24 pmol) was added to a solution of 10-mer 5'-azide-linked, 3'-biotinylated template (12 pmol) in 100 mM CAPS buffer (pH 10) with 500 mM NaCl. The mixture was agitated at 25° C. for 0.5 h then at 37° C. for 12 h. The biotinylated products and unreacted templates were purified by treating the reaction mixture with streptavidin-linked magnetic particles (Roche) and eluted following the manufacturer's protocol. DNA in the eluant was precipitated with ethanol and glycogen. Substrates 11-12 were subjected directly to subsequent mass spectroscopic analysis. Samples for MALDI-TOF analysis were prepared by desalting the pellets dissolved in the matrix solution using a ZipTip C18 column (millipore).

The resulting iminophosphoranes were identified by MALDI-TOF mass spectrometry and to be unexpectedly stable to hydrolysis especially under acidic conditions, presumably due to formation of a stable HCl salt (Shalev, et al. (1996) J. ORG. CHEM. 61: 1689-1701). Treatment of template-linked azides with DNA-linked phosphine in pH 10 buffer at 25° C. for 0.5 h followed by 37° C. for 12 h, however, resulted in quantitative iminophosphorane hydrolysis to generate the corresponding primary amines.

The results from the MALDI-TOF analysis are summarized in Table 1 where reagents 1-12 are denoted as in FIG. 5B. Due to the instability under the conditions for MALDI-TOF experiments, thiol-linked products (11-12) were captured as alkyl thioether adducts by treating with iodoacetamide (5 mM) following the DNA-templated Staudinger reaction (the MALDI-TOF data for 11-12 in Table 1 are of captured thioether adducts).

TABLE 1

| Reagents (see, FIG. 5B) | Expected Mass | Observed Mass |
|---|---|---|
| 1 | 5866.05 | 5868.02 ± 9 |
| 2 | 5922.16 | 5926.50 ± 9 |
| 3 | 5942.15 | 5945.18 ± 9 |
| 4 | 5937.13 | 5940.98 ± 9 |
| 5 | 5934.17 | 5934.61 ± 9 |
| 6 | 5942.15 | 5944.46 ± 9 |
| 7 | 5928.12 | 5930.91 ± 9 |
| 8 | 5963.16 | 5968.42 ± 9 |
| 9 | 5909.07 | 5915.97 ± 9 |
| 10 | 6032.23 | 6038.24 ± 9 |
| 11 | 5941.16 | 5944.61 ± 9 |
| 12 | 5955.19 | 5957.01 ± 9 |

Figure 7:
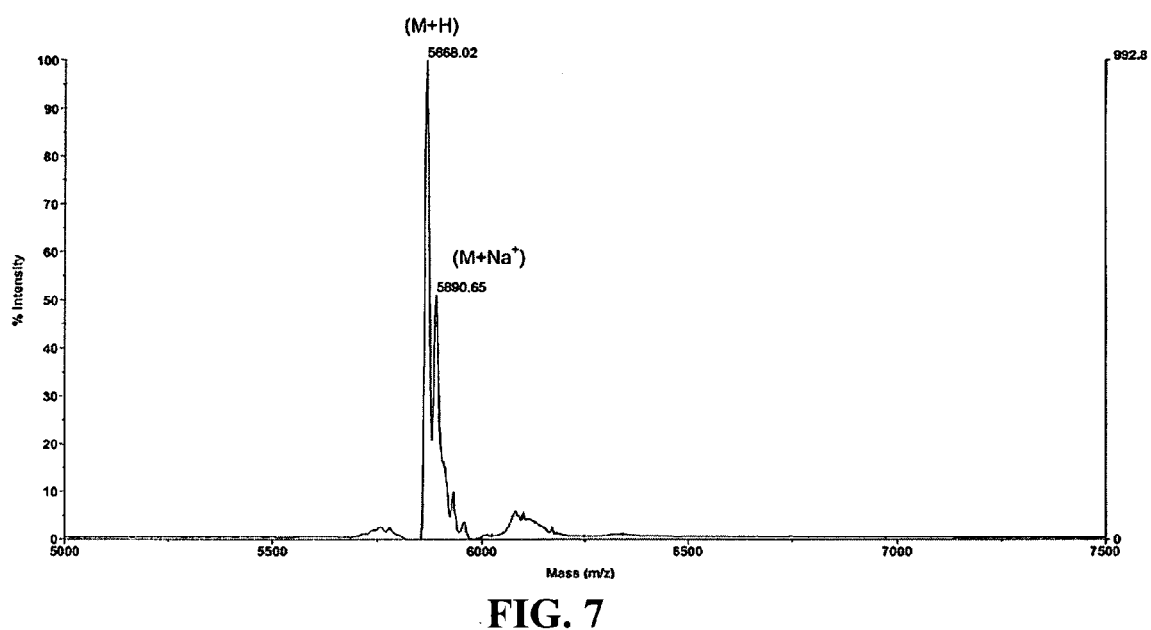
FIG. 7 is a representative MALDI-TOF spectrum from a DNA-templated functional group transformation (in this case, the amine product arising from azide 1).

Mass spectrometric analysis of azide reduction reactions was consistent in each case with the formation of expected primary amine products. A representative spectrum is shown in FIG. 7.

Based on the mass spectroscopic analyses set forth in Table 1, the sequence specific azide-to-amine, azide-to-carboxylic acid, and azide-to-thiol transformations all produced the appropriate products.

Example 3

Transformations of Amine-Linked Templates Using Small Molecule Reagents

To further explore the ability of DNA-templated functional group transformations to enable-DNA-linked reagents to participate in sequence-programmed synthesis, four DNA (templates 13-16, FIG. 8) were prepared, each containing a different azide at the 5' terminus, one of four unique six-base codons, and a biotin group at the 3' terminus to facilitate template manipulation and purification. The azide-linked templates then were chemically converted into amine-linked templates by exposure to TCEP-HCl. The resulting amines then were reacted with free reagents to determine whether the conversion of the amine intermediate into a final product was possible. In particular, dansyl chloride (21), ethyl chloroformate (22), 4-methoxy phenyl isocyanate (23) and 6-morpholino pyridinyl 3-isothiocyanate (24) were all chosen amine-reactive agents as they cannot easily be attached to DNA due to their structure or their reactivity with water. Simplified reaction schemes showing the starting reagents and theoretical end products are shown in FIG. 9.

I. Materials and Methods
Coding sequences for the templates were designed by computational screening to (i) ensure that at least 6 non-complementary base pairs existed between any two different codons, (ii) maintain a constant % GC per codon in order to minimize differences in melting temperatures between reagents, and (iii) vary in mass such that the molecular weights of the 16 theoretical small-molecule coupling products are distinct and identifiable by MALDI-TOF mass spectrometry.

Figure 8:
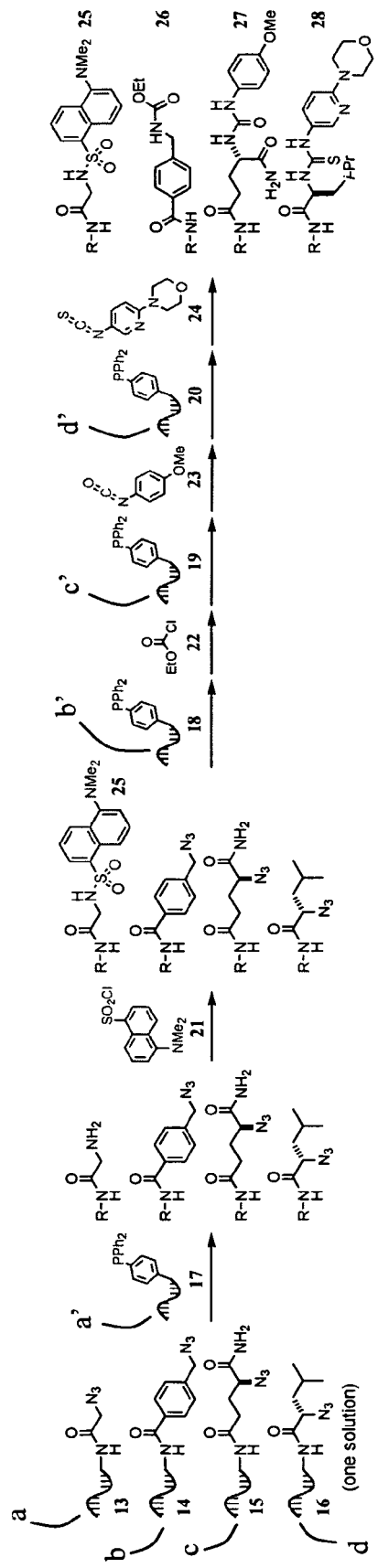
FIG. 8 depicts a reaction of a single solution containing four azides with four non-DNA-linked small-molecule electrophiles to generate four sequence-programmed sulfonamide, carbamate, urea, and thiourea products. Template 13 is attached to an oligonucleotide having codon sequence a. The triphenylphosphine containing transfer unit 17 is attached to an oligonucleotide having anti-codon sequence a'. During templated synthesis codon sequence a anneals to anti-codon sequence a'. Similarly, templates 14, 15, and 16 contain codon sequences b, c, and d, respectively, which anneal to transfer units 18, 19, and 20 via anti-codon sequences b', c', and d', respectively.
Figure 9:
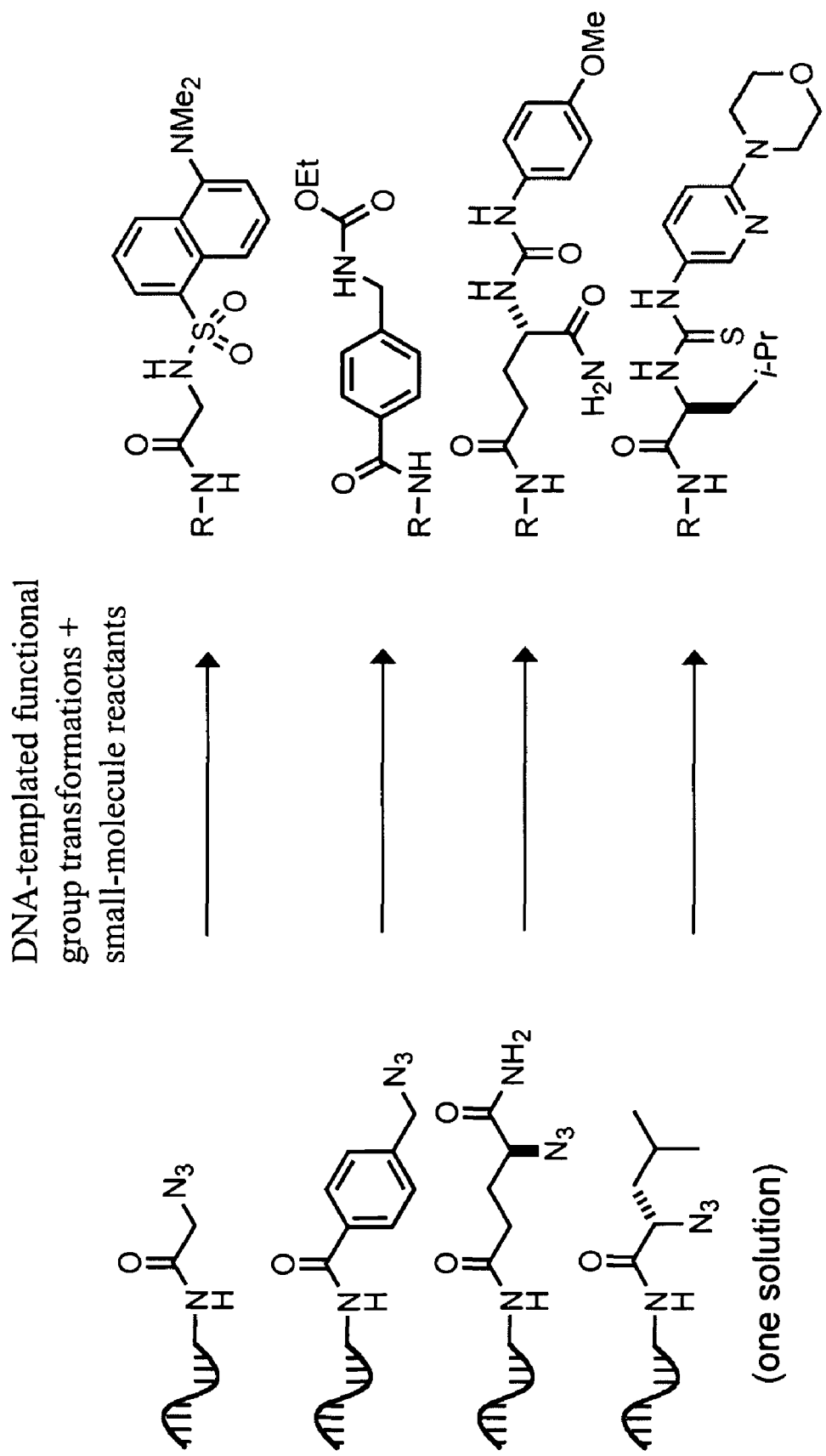
FIG. 9 is a schematic illustration showing the starting reagents used and reaction products created in FIG. 8.

Each of the templates used in the schemes shown in FIG. 8 (templates 13-16) contained 5' $NH_2(C_2H_4O)_2$—$PO_3H$-TT-(codon)-$GTA_n$-$OPO_3H$—$CH(CH_2OH)CH_2(OC_2H_4)_4$ $CH_2NHCO$-biotin. The codons used for each template were as follows: the codon for template 13 was GTG CAA CGT CAT, n=0 (SEQ ID NO: 6); the codon for template 14 was CCT AGT COT CAT, n=3 (SEQ ID NO: 7); the codon for template 15 was TAA GCC COT CAT, n=2 (SEQ ID NO: 8); and the codon for template 16: AGC TTG COT CAT, n=1 (SEQ ID NO: 9).

The azide-containing templates 13-16, were prepared as described in Example 1 (see templates 1, 3, 4, and 2, respectively).

The azide groups in templates 13-16 were chemically transformed into amine groups by exposure to TCEP-HCl. Briefly, amine-linked templates then were prepared by treating the azide-linked templates (templates 13-16) with 5 mM TCEP-HCl in 100 mM MOPS buffer (pH 7.5) at 25° C. for 3 h. The resulting templates were purified by HPLC. Thereafter, the resulting templates (amine intermediates) were reacted with soluble reagents to determine whether functional group transformations were possible.

II. Results and Conclusions

Once the amine-linked templates 13-16 were created, they were then exposed to soluble reagents to see whether functional group transformations were possible. Each of the transformations are discussed in detail below.

Figure 10A:
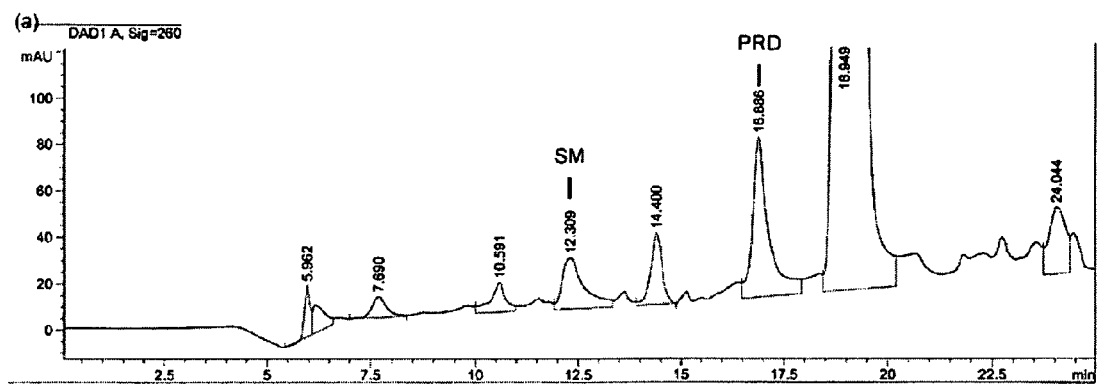
FIG. 10A through FIG. 10D are drawings of HPLC traces (monitored at 260 nm) following HPLC analysis of reactions of amine-linked templates with small-molecule reagents. SM indicates unreacted starting material amine-linked template peaks. PRD indicates derivatized products. Unless otherwise noted, peaks other than those labeled as SM or PRD do not correspond to DNA-linked species as judged by UV absorption at 230 nm and by MALDI-TOF analysis.

The amine-linked template 13 (400 pmol) in 100 μL of 100 mM aqueous $NaHCO_3$ (pH 9.0) was mixed with 20 mM dansyl chloride 21 in 100 μL DMF and agitated at 37° C. for 1 h. The reaction mixture was diluted in 200 μL 0.1 M TEAA and passed through a NAP-5 size exclusion column. The eluant in 1 mL 0.1 M TEAA was analyzed by analytical scale reverse phase HPLC (8-30% MeCN/0.1 M TEAA gradient). Product yield was calculated based on the integrated peak areas (based on UV absorbance at 260 nm) of the starting material, the product, and any side products. A representative chromatogram is shown in FIG. 10A.

Figure 10B:
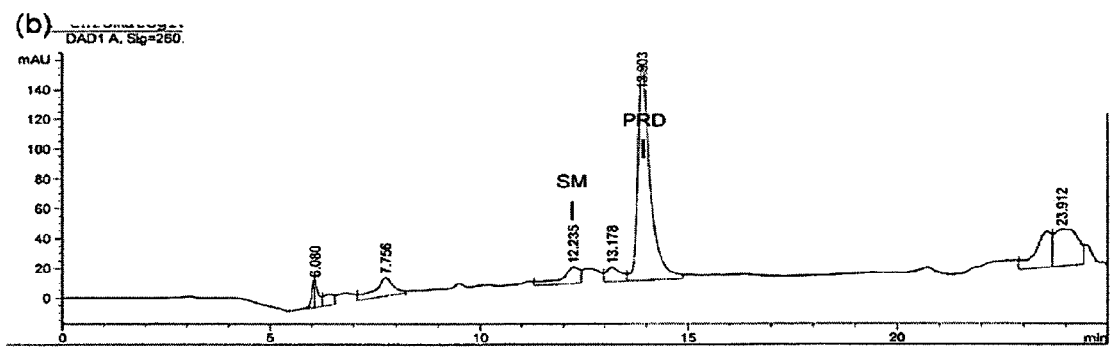

Amine-linked template 14 (400 pmol) in 100 μL of 200 mM aqueous $NaHCO_3$ (pH 9.0) was mixed with 40 mM ethyl chloroformate 22 in 100 μL DMF and agitated at 37° C. for 1 h. The reaction was quenched by addition of glycogen in NaOAc buffer (pH 5.0) followed by ethanol precipitation. The pellet was dissolved in 0.1 M TEAA and analyzed by analytical scale reverse phase HPLC (8-30% MeCN/0.1 M TEAA gradient). A representative chromatogram is shown in FIG. 10B.

Figure 10C:
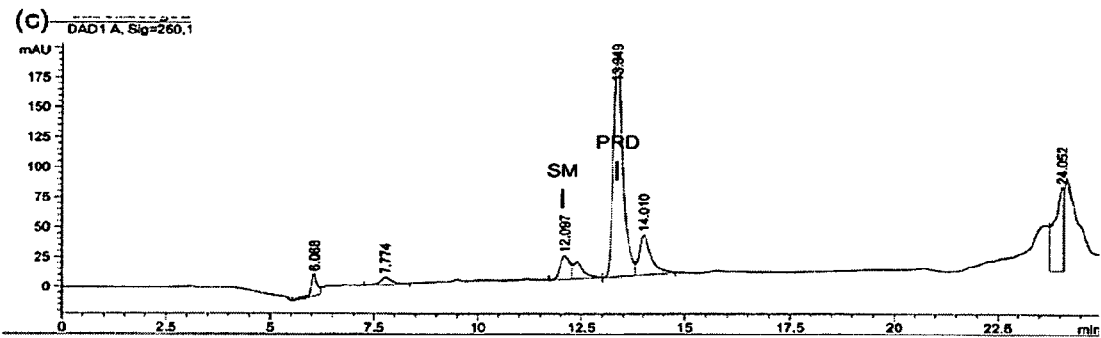

Amine-linked template 15 (400 pmol) in 100 μL of 500 mM aqueous triethylamine (pH 10) was mixed with 20 mM 4-methoxyphenylisocyanate 23 in 100 μL DMF and agitated at 37° C. for 1 h. The reaction mixture was quenched and analyzed as described above. A representative chromatogram is shown in FIG. 10C.

Figure 10D:
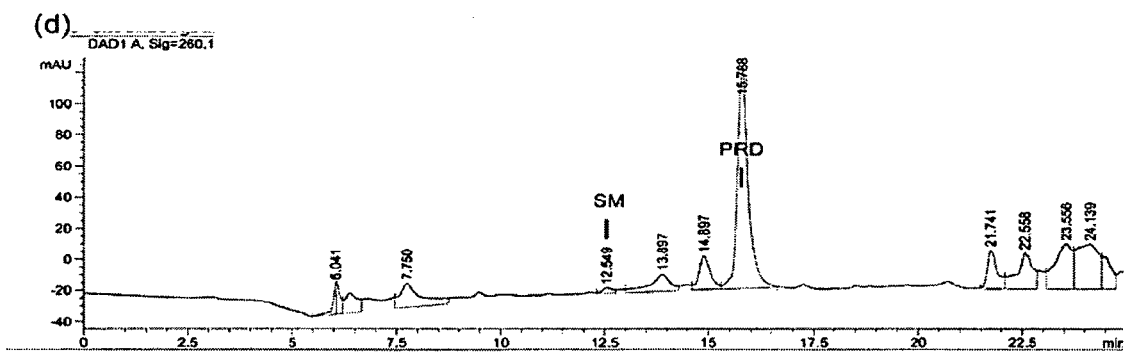

Amine-linked template 16 (400 pmol) in 100 μL of 500 mM aqueous triethylamine (pH 10) was mixed with 20 mM and was allowed to react with 20 mM 6-morpholino isothiocyanate 24 in 100 μL DMF and agitated at 37° C. for 1 h. The reaction mixture was quenched and analyzed as described above. A representative chromatogram is shown in FIG. 10D.

When soluble reagents (free reactants) 21, 22, 23, or 24 were added in excess (10 or 20 mM final concentration) in DMF to a template-linked primary amine under basic conditions (pH 9-10), the corresponding sulfonamide, carbamate, urea, or thiourea was efficiently generated (70% yield for 21, >86% for 22, 23 and 24). These results demonstrated that it was possible to convert a template coupled to an amide into a sulfonamide, a carbomate, urea or thiourea using free reactants.

Example 4

Sequence Specific Transformation of Four Azide-Linked Templates Using Small Molecule Reagents This Example demonstrates that it is possible to perform a sequence specific transformation of template bound reactants to generate reaction intermediates, which can then be reacted with free reactants to produce reaction products. In particular, a single-solution mixture of azide linked templates were sequence-specifically transformed into amine intermediates. The amine intermediates were then sequence-specifically modified into sulfonamide, carbamate, urea, and thiourea products using sulfonyl chloride, chloroformate, isocyanate, and isothiocyanate reactants not linked to DNA.

I. Materials and Methods
(i) Preparation of Functionalized Oligonucleotides
(a) Template Oligonucleotides
The templates 13-16 were prepared as described in Example 3.
(b) Transfer Units
Each of the following triphenylphosphine-linked oligonucleotides were prepared as described in Example 1.

Oligonucleotide 17 (FIG. 9) had the structure 5' CGT TGC ACA A-$OPO_3H$—$CH_2CH(CH_2OH)(CH_2)_4$ $NHCOC_6H_4PPh_2$ (SEQ ID NO: 10). Oligonucleotide 18 (FIG. 9) had the structure 5' CGA CTA GGA A-$OPO_3H$—$CH_2CH(CH_2OH)(CH_2)_4NHCOC_6H_4PPh_2$ (SEQ ID NO: 11). Oligonucleotide 19 (FIG. 9) had the structure 5' CGG GCT TAA A-$OPO_3H$—$CH_2CH(CH_2OH)(CH_2)_4$ $NHCOC_6H_4PPh_2$ (SEQ ID NO: 12). Oligonucleotide 20 (FIG. 9) had the structure 5' CGC AAG CTA A-$OPO_3H$—$CH_2CH(CH_2OH)(CH_2)_4NHCOC_6H_4PPh_2$ (SEQ ID NO: 13).

II. Results and Conclusions

A mixture of templates 13-16 was combined with sequence specific reactant 17 and then free reactant 21. The resulting solution was similarly combined with sequence specific reactant 18 followed by free reactant 22; sequence specific reactant 19 followed by free reactant 23; and sequence specific reactant 20 followed by free reactant 24.

More specifically, 3' triphenylphosphine-linked oligonucleotide 17 (8 equiv.) was added to a single solution mixture of the four 5' azide-linked templates (templates 13-16, 100 nM for each template) in 100 mM CAPS buffer (pH 10) and 500 mM NaCl to effect azide-to-amine transformation. The mixture was incubated at 25° C. for 0.5 h then 37° C. for 12 h. The oligonucleotides were precipitated by the addition of glycogen in NaOAc buffer (pH 5.0) and ethanol. The pellet was dissolved in 100 μL of 100 mM $NaHCO_3$ and was allowed to react with dansyl chloride 21 in 100 μL of DMF (20 mM) at 37° C. for 1 h. The reaction mixture was desalted by ethanol precipitation. If the DNA-templated azide-to-amine transformation proceeded sequence-specifically, only the amine arising from template 13 should react with sequence specific reactant 21 to generate sulfonamide 25, while templates 14-16 should remain unaltered (see, FIG. 8). Excess sulfonyl chloride was removed upon ethanol precipitation, and any unreacted amines were removed using N-hydroxysuccinimidyl (NHS) ester-linked resin.

The DNA-templated azide-to-amine transformation described above then was repeated using phosphine-linked oligonucleotide 18. The pellet was dissolved in 100 μL of 200 mM NaHCO₃ and was allowed to react with ethyl chloroformate 22 in 100 μL of DMF (40 mM) at 37° C. for 1 h. The reaction mixture was desalted by ethanol precipitation and dried.

The DNA-templated azide-to-amine transformation described above then was repeated using phosphine-linked oligonucleotide 19. The pellet was dissolved in 100 μL of 500 mM aqueous triethylamine solution and was allowed to react with 4-methoxyphenylisocyanate 23 in 100 μL of DMF (20 mM) at 37° C. for 1 h. The reaction mixture was desalted by ethanol precipitation and dried.

The DNA-templated azide-to-amine transformation described above then was repeated using phosphine-linked oligonucleotide 20. The pellet was dissolved in 100 μL of 500 mM aqueous triethylamine solution and was allowed to react with 6-morpholino-3-pyridinylisothiocyanate 24 in 100 μL of DMF (20 mM) at 37° C. for 1 h. The reaction mixture was desalted by ethanol precipitation and dried. The pellet was dissolved in 100 mM MES buffer (pH 6), first treated with TCEP-HCl (5 mM) at 25° C. for 2 h then with NHS activated resin (Amersham Biosciences; 5 μL resin solution for 100 pmol template) for another 2 h. The resin was removed by filtration and washed three times with 0.1 M TEAA.

Figure 11B:
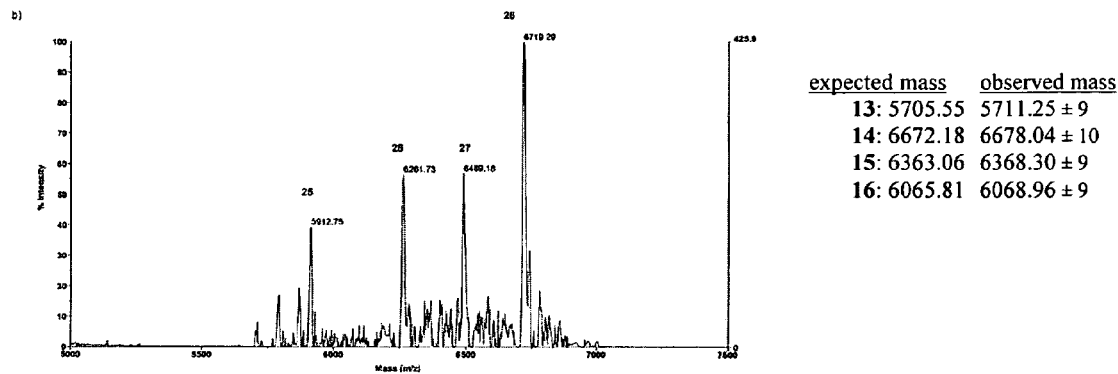
FIG. 11B shows a MALDI-TOF spectrum of the four sequence-specific transformation products (products 25-28 in FIG. 8) of the azide starting materials 13-16.
Figure 11A:
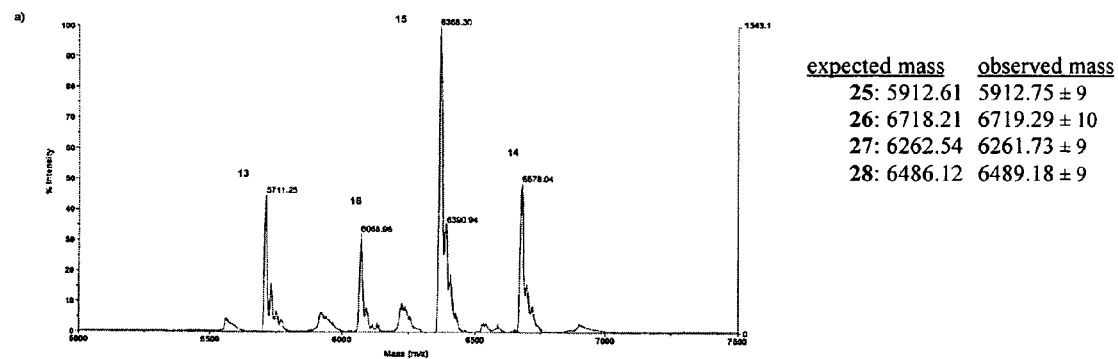
FIG. 11A shows a MALDI-TOF spectrum of the four azide starting materials in one solution (reagents 13-16 in FIG. 8).

The final mixture of products was purified by capturing template-linked biotin groups with streptavidin linked to magnetic particles. The captured oligonucleotides were eluted from the particles following the manufacturer's protocol. The DNA in the eluant was precipitated with NaOAc (pH 5.0), glycogen, and ethanol. DNA recovery was determined spectrometrically by monitoring UV absorbance for the starting material pool and the final product pool at 260 nm. The concentration for a mixture containing equal amounts of products 25-28 (see, FIG. 8) with a UV absorbance of 1.0 at 260 nm was estimated to be 5.5 μM. Samples for MALDI-TOF analysis were prepared as described in Example 2. FIG. 11A and FIG. 11B show representative spectra of starting materials (templates 13, 14, 15 and 16) and products (products 25, 26, 27, 28), respectively.

MALDI-TOF mass spectrometry revealed that the final product mixture contained predominantly the four sequence-programmed products (sulfonamide 25, carbamate 26, urea 27, and thiourea 28). None of the 12 possible undesired cross-products were observed.

UV spectrometry analysis indicated that the final product mixture was generated in 51% overall yield for the four consecutive DNA-templated reduction and small-molecule coupling sequences. These results establish that DNA-templated functional group transformations enable non-DNA-linked small molecules to participate in sequence-programmed reactions. The efficiency of this process also highlights the value of molecular biology-based purification and washing strategies made possible when performing organic synthesis on this minute (sub-nmol) scale.

Taken together, the DNA-templated functional group transformation described in this Example expands the synthetic capabilities of nucleic acid-templated synthesis by addressing the need for reagents to be tethered to oligonucleotides. When the linkage of reagents to oligonucleotides is not possible or is inconvenient, these transformations allow such reagents to nevertheless contribute to small molecule syntheses while preserving the correspondence between an oligonucleotide sequence and a product structure.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of synthesizing a reaction product by nucleic acid-templated synthesis, the method comprising the steps of:
    (a) providing a mixture comprising a plurality of different first reactive units each attached to corresponding different first oligonucleotides comprising a codon sequence, wherein each oligonucleotide sequence is indicative of the first reactive unit attached thereto;
    (b) providing a second reactive unit attached to a second oligonucleotide comprising an anti-codon sequence complementary to the codon sequence of at least one first oligonucleotide attached to a first reactive unit;
    (c) annealing the codon sequence of at least one of the first oligonucleotides with the anti-codon sequence of the second oligonucleotide to induce a reaction between the first and second reactive units to form a first reaction intermediate covalently attached at least to a first oligonucleotide; and
    (d) after step (c), combining the first reaction intermediate, co-existing with at least one of the reactive units, with a free reactant selectively reactive with the first reaction intermediate thereby synthesizing a first reaction product attached to the first oligonucleotide, wherein the free reactant (i) is not present during any of steps (a), (b) or (c); and (ii) is more reactive with the first reaction intermediate than with at least one of the reactive units in the mixture.

2. The method of claim 1, further comprising the steps of:
    (e) providing a third reactive unit attached to a third oligonucleotide comprising an anti-codon sequence complementary to the codon sequence of at least one first reactive unit;
    (f) annealing the codon sequence of at least one of the first oligonucleotides with the anti-codon sequence of the third oligonucleotide to induce a reaction between the first and third reactive units to form a second reaction intermediate attached to the at least one of the first oligonucleotides; and
    (g) after step (f), combining the second reaction intermediate with a free reactant selectively reactive with the second reaction intermediate thereby synthesizing a second reaction product attached to the at least one of the first oligonucleotides, wherein the free reactant selectively reactive with the second reaction intermediate (i) is not present during any of steps (a), (b), (c), (d), (e) or (f); and (ii) is more reactive with the second reaction intermediate than with at least one of the reactive units in the mixture.

3. The method of claim 1, wherein the free reactant is at least five times more reactive with the reaction intermediate than with either of the reactive units in the starting mixture.

4. The method of claim 1, wherein the free reactant is at least fifty times more reactive with the reaction intermediate than with at least one of the reactive units in the starting mixture.

5. The method of claim 1, wherein the free reactant is at least one thousand times more reactive with the reaction intermediate than with at least one of the reactive units in the starting mixture.

6. The method of claim 1, wherein the reaction product is synthesized with a yield greater than or equal to 50%.

7. An in vitro method of performing nucleic acid-templated synthesis, the method comprising the steps of:
  (a) providing a mixture comprising (i) a plurality of different templates each comprising a first reactive unit covalently attached to a first oligonucleotide defining a codon sequence, and (ii) a transfer unit comprising a second reactive unit covalently attached to a second oligonucleotide defining an anti-codon sequence complementary to the codon sequence of the template;
  (b) annealing the codon sequence of one template with the anti-codon sequence of the transfer unit to bring the first reactive unit and the second reactive unit into reactive proximity so that the first and second reactive units react with one another to produce a reaction intermediate; and
  (c) after step (b), contacting the reaction intermediate, while co-existing with unreacted template, with a free reactant, which chemically reacts with the reaction intermediate to produce a reaction product, wherein the free reactant (i) is not present during any of steps (a) or (b); and (ii) is more reactive with the reaction intermediate than with at least one of the reactive units in the mixture and wherein the first oligonucleotide remains attached to the reaction product.

8. The method of claim 7, wherein the first reactive unit is a small molecule scaffold.

9. The method of claim 7, wherein, in step (b), a functional group of the first reactive unit is transformed into a different chemical moiety in the reaction intermediate.

10. The method of claim 8, wherein the small molecule scaffold contains a protected functional group.

11. The method of claim 10, wherein, in step (b), the functional group is deprotected to produce a reaction intermediate where the small molecule scaffold contains a deprotected functional group.

12. The method of claim 7, wherein the reaction product is not a nucleic acid.

13. The method of claim 7, wherein the reaction product is not a nucleotide or a nucleotide analog.

14. The method of claim 7, wherein, in step (b), the first and second reactive units react with one another to produce the reaction intermediate without the assistance of a ribosome.

15. The method of claim 7 further comprising the step of selecting the reaction product attached to the first oligonucleotide.

16. The method of claim 15 further comprising the step of amplifying the first oligonucleotide.

17. The method of claim 16 comprising the additional step of determining the sequence of the first oligonucleotide attached to the reaction product so as to determine the identity or synthetic history of the reaction product.

* * * * *

UNITED STATES PATENT AND TRADEMARK OFFICE
CERTIFICATE OF CORRECTION

PATENT NO. : 8,017,323 B2
APPLICATION NO. : 11/336405
DATED : September 13, 2011
INVENTOR(S) : David R. Liu et al.

It is certified that error appears in the above-identified patent and that said Letters Patent is hereby corrected as shown below:

In the Specification

At Column 1, Lines 13-16, please change the paragraph:
"This invention was made with Government support under the Office of Naval Research award N00014-03-1-0749 and the National Institutes of Health award R01 GM065865. The United States Government has certain rights in the invention."

To:
-- This invention was made with government support under N00014-00-1-0596 and N00014-03-1-0749 awarded by U.S. Office of Naval Research (NAVY/ONR) and under GM065865 awarded by National Institutes of Health (NIH). The government has certain rights in the invention. --

Signed and Sealed this
Ninth Day of September, 2025

Coke Morgan Stewart
*Acting Director of the United States Patent and Trademark Office*

SEQUENCE LISTING

```
<160> NUMBER OF SEQ ID NOS: 13

<210> SEQ ID NO 1
<211> LENGTH: 30
<212> TYPE: DNA
<213> ORGANISM: Artificial
<220> FEATURE:
<223> OTHER INFORMATION: 30-mer Oligonucleotide Template (for
      Characterization by PAGE)

<400> SEQUENCE: 1
ggtacgaatt gcactcggga aatccacctt                                      30

<210> SEQ ID NO 2
<211> LENGTH: 10
<212> TYPE: DNA
<213> ORGANISM: Artificial
<220> FEATURE:
<223> OTHER INFORMATION: 10-mer Oligonucleotide Linked to Phosphine

<400> SEQUENCE: 2
aattcgtacc                                                            10
```

```
<210> SEQ ID NO 3
<211> LENGTH: 10
<212> TYPE: DNA
<213> ORGANISM: Artificial
<220> FEATURE:
<223> OTHER INFORMATION: 10-mer Oligonucleotide with three-base mismatch

<400> SEQUENCE: 3
aatacatccc                                                          10

<210> SEQ ID NO 4
<211> LENGTH: 20
<212> TYPE: DNA
<213> ORGANISM: Artificial
<220> FEATURE:
<223> OTHER INFORMATION: 20-mer Oligonucleotide Capture Reagent

<400> SEQUENCE: 4
tcccgagtgc aattcgtacc                                               20

<210> SEQ ID NO 5
<211> LENGTH: 10
<212> TYPE: DNA
<213> ORGANISM: Artificial
<220> FEATURE:
<223> OTHER INFORMATION: 10-mer Oligonucleotide Template (for
      Characterization by Mass Spetroscopy)

<400> SEQUENCE: 5
ggtacgaatt                                                          10

<210> SEQ ID NO 6
<211> LENGTH: 14
<212> TYPE: DNA
<213> ORGANISM: Artificial
<220> FEATURE:
<223> OTHER INFORMATION: Template 13 Oligonucleotide

<400> SEQUENCE: 6
ttgtgcaacg tcat                                                     14

<210> SEQ ID NO 7
<211> LENGTH: 23
<212> TYPE: DNA
<213> ORGANISM: Artificial
<220> FEATURE:
<223> OTHER INFORMATION: Template 14 Oligonucleotide

<400> SEQUENCE: 7
ttcctagtcg tcatgtagta gta                                           23

<210> SEQ ID NO 8
<211> LENGTH: 20
<212> TYPE: DNA
<213> ORGANISM: Artificial
<220> FEATURE:
<223> OTHER INFORMATION: Template 15 Oligonucleotide

<400> SEQUENCE: 8
tttaagcccg tcatgtagta                                               20

<210> SEQ ID NO 9
<211> LENGTH: 17
<212> TYPE: DNA
<213> ORGANISM: Artificial
<220> FEATURE:
```

```
<223> OTHER INFORMATION: Template 16 Oligonucleotide

<400> SEQUENCE: 9
ttagcttgcg tcatgta                                                     17

<210> SEQ ID NO 10
<211> LENGTH: 10
<212> TYPE: DNA
<213> ORGANISM: Artificial
<220> FEATURE:
<223> OTHER INFORMATION: Reactant 17 Oligonucleotide

<400> SEQUENCE: 10
cgttgcacaa                                                             10

<210> SEQ ID NO 11
<211> LENGTH: 10
<212> TYPE: DNA
<213> ORGANISM: Artificial
<220> FEATURE:
<223> OTHER INFORMATION: Reactant 18 Oligonucleotide

<400> SEQUENCE: 11
cgactaggaa                                                             10

<210> SEQ ID NO 12
<211> LENGTH: 10
<212> TYPE: DNA
<213> ORGANISM: Artificial
<220> FEATURE:
<223> OTHER INFORMATION: Reactant 19 Oligonucleotide

<400> SEQUENCE: 12
cgggcttaaa                                                             10

<210> SEQ ID NO 13
<211> LENGTH: 10
<212> TYPE: DNA
<213> ORGANISM: Artificial
<220> FEATURE:
<223> OTHER INFORMATION: Reactant 20 Oligonucleotide

<400> SEQUENCE: 13
cgcaagctaa                                                             10
```